(12) United States Patent
Farritor et al.

(10) Patent No.: US 8,974,440 B2
(45) Date of Patent: Mar. 10, 2015

(54) MODULAR AND COOPERATIVE MEDICAL DEVICES AND RELATED SYSTEMS AND METHODS

(75) Inventors: Shane M. Farritor, Lincoln, NE (US); Mark Rentschler, Boulder, CO (US); Amy Lehman, Seward, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 1272 days.

(21) Appl. No.: 12/192,779

(22) Filed: Aug. 15, 2008

(65) Prior Publication Data

US 2009/0048612 A1 Feb. 19, 2009

Related U.S. Application Data

(60) Provisional application No. 60/956,032, filed on Aug. 15, 2007, provisional application No. 60/990,076, filed on Nov. 26, 2007, provisional application No. 60/990,106, filed on Nov. 26, 2007, provisional application No. 61/025,346, filed on Feb. 1, 2008, provisional application No. 61/030,617, filed on Feb. 22, 2008.

(51) Int. Cl.
*A61B 17/00* (2006.01)
*A61B 19/00* (2006.01)
(52) U.S. Cl.
CPC ..... *A61B 19/2203* (2013.01); *A61B 2019/2215* (2013.01); *A61B 2019/5229* (2013.01)
USPC ............................................. 606/1

(58) Field of Classification Search
CPC ............... A61B 19/22; A61B 19/2203; A61B 2019/2242
USPC ............................................. 606/1
See application file for complete search history.

(56) References Cited

U.S. PATENT DOCUMENTS

| 3,870,264 | A | 3/1975 | Robinson |
| 3,989,952 | A | 11/1976 | Timberlake et al. |
| 4,246,661 | A | 1/1981 | Pinson |
| 4,258,716 | A | 3/1981 | Sutherland |

(Continued)

FOREIGN PATENT DOCUMENTS

| EP | 2286756 A1 | 2/2011 |
| JP | 2004144533 | 5/1990 |

(Continued)

OTHER PUBLICATIONS

Tendick et al., "Applications of Micromechatronics in Minimally Invasive Surgery," IEEE/ASME Transactions on Mechatronics, 1998; 3(1): 34-42.

(Continued)

*Primary Examiner* — William Thomson
*Assistant Examiner* — John R Downey
(74) *Attorney, Agent, or Firm* — Davis, Brown, Koehn, Shors & Roberts, P.C.; Sean D. Solberg

(57) ABSTRACT

The various embodiments disclosed herein relate to modular medical devices, including various devices with detachable modular components and various devices with pivotally attached modular components. Additional embodiments relate to procedures in which various of the devices are used cooperatively. Certain embodiments of the medical devices are robotic in vivo devices.

20 Claims, 19 Drawing Sheets

(56) References Cited

U.S. PATENT DOCUMENTS

| | | | |
|---|---|---|---|
| 4,278,077 A | 7/1981 | Mizumoto |
| 4,538,594 A | 9/1985 | Boebel et al. |
| 4,568,311 A | 2/1986 | Miyaki |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,398 A * | 4/1997 | Smith et al. ............... 604/95.01 |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,900 A | 8/1998 | Madhani et al. |
| 5,807,377 A | 9/1998 | Madhani et al. |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,911,036 A | 6/1999 | Wright et al. |
| 5,971,976 A | 10/1999 | Wang et al. |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Okamoto et al. |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Tierney et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |

(56) References Cited

U.S. PATENT DOCUMENTS

| | | |
|---|---|---|
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,179,073 B2 | 5/2012 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0026186 A1 | 2/2002 | Woloszka et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |

(56) References Cited

U.S. PATENT DOCUMENTS

| | | |
|---|---|---|
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0106916 A1 | 6/2004 | Quaid et al. |
| 2004/0111113 A1 | 6/2004 | Nakamura et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola et al. |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0164079 A1 | 7/2008 | Jacobsen |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Scott |
| 2010/0204713 A1 | 8/2010 | Ruiz |
| 2010/0245549 A1 | 9/2010 | Allen et al. |
| 2010/0262162 A1 | 10/2010 | Omori |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0077478 A1 | 3/2011 | Freeman et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0253515 A1 | 10/2012 | Coste-Maniere et al. |
| 2013/0041360 A1 | 2/2013 | Farritor |
| 2013/0131695 A1 | 5/2013 | Scarfogliero et al. |

FOREIGN PATENT DOCUMENTS

| | | |
|---|---|---|
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2003220065 | 8/2003 |
| JP | 2004322310 | 6/2004 |

(56) References Cited

FOREIGN PATENT DOCUMENTS

| | | |
|---|---|---|
| JP | 2004180781 | 7/2004 |
| JP | 2004329292 | 11/2004 |
| JP | 2006508049 | 3/2006 |
| JP | 2007-181682 A | 7/2007 |
| WO | WO 92/21291 | 12/1992 |
| WO | WO 02/082979 | 10/2002 |
| WO | WO 02/100256 | 12/2002 |
| WO | WO 2005/009211 | 7/2004 |
| WO | WO 2006/052927 | 8/2005 |
| WO | WO 2006 005075 | 1/2006 |
| WO | WO 2006/079108 | 1/2006 |
| WO | WO 2007/111571 | 10/2007 |
| WO | WO 2007/149559 | 12/2007 |
| WO | WO 2009023851 A1 | 8/2008 |
| WO | WO 2009/144729 | 12/2009 |
| WO | WO2010/042611 | 4/2010 |
| WO | WO2010/046823 | 4/2010 |
| WO | WO 2011/118646 A1 | 9/2011 |
| WO | WO 2011/135503 A1 | 11/2011 |
| WO | WO 2013009887 | 1/2013 |

OTHER PUBLICATIONS

Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imagining," vol. 25, No. 1, Gastroenterology Nursing, pp. 24-27.
International Search Report and Written Opinion of international application No. PCT/US2010/061137, mailed Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., Wireless endoscopy, Gastrointestinal Endoscopy 2000; 51(6): 725-729.
Hanly et al., "Value of the SAGES Learning Center in introducing new technology," Surgical Endoscopy, 2004; 19 (4): 477-483.
Hanly et al., "Robotic Abdominal Surgery," The American Journal of Surgery 188 (Suppl.to Oct. 1994): 19S-26S, 2004.
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.

Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on Computational Intelligence, Robotics and Autonomous Systems (CIRAS 2001), Nov. 28-30, 2001, Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, 1 pg.
Preliminary Amendment filed Apr. 11, 2007, in related case U.S. Appl. No. 11/403,756, 7 pp.
Preliminary Amendment filed Jul. 30, 2008, in related case U.S. Appl. No. 12/171,413, 4 pp.
RCE and Amendment filed Jun. 13, 2007, in related case U.S. Appl. No. 11/403,756, 8 pp.
Rentschler et al., "Mobile in Vivo Biopsy and Camera Robot," Studies in Health and Infonnatics Medicine Meets Virtual Reality, vol. 119., pp. 449-454, IOS Press, Long Beach, CA, 2006e.
Rentschler et al., Mobile in Vivo Biopsy Robot, IEEE International Conference on Robotics and Automation, Orlando, Florida, May 2006, pp. 4155-4160.
Rentschler et al., "Miniature in vivo Robots for Remote and Harsh Environments," IEEE Transactions on Information Technology in Biomedicine, Jan. 2006; 12(1): 66-75.
Rentschler et al., "An in Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, I pg.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Mechanical Design of Robotic in Vivo Wheeled Mobility," ASME Journal of Mechanical Design, 2006a, pp. I-II.
Rentschler et al., "Mobile in Vivo Camera Robots Provide Sole Visual Feedback for Abdominal Exploration and Cholecystectomy," Journal of Surgical Endoscopy, 20-I: 135-138, 2006b.
Rentschler et al., "Mobile in Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of in Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of in Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward in Vivo Mobility," Studies in Health Technology and Infonnatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleopserated Endoscopic, Grasper for Minimally Invasive Surgery-Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Informa-

(56) References Cited

OTHER PUBLICATIONS tion and Tool/Tissue Interactions," Studies in Health Technology and Informatics-Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Informatics-Medicine Meets Virtual Reality, pp. 442-448, Jan. 2005.
Rosen et al., "Task Decomposition of Laparoscopic Surgery for Objective Evaluation of Surgical Residents Learning Curve Using Hidden Markov Model," Computer Aided Surgery, vol. 7, pp. 49-61, 2002.
Rosen et al., "The Blue Dragon—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fantastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
International Preliminary Report on Patentability from related case PCT/US2007/014567, mailed Jan. 8, 2009, 11 pp.
International Search report and Written Opinion from international application No. PCT/US2012/41911, mailed Mar. 13, 2013.
International Search Report and Written Opinion from international application No. PCT/US12/46274, mailed Sep. 25, 2012.
International Search Report and Written Opinion from international application No. PCT/US2007/089191, mailed Nov. 10, 2008, 20 pp.
International Search Report and Written Opinion from international application No. PCT/US07/14567, mailed Apr. 28, 2008, 19 pp.
International Search Report and Written Opinion of international application No. PCT/US2008/069822, mailed Aug. 5, 2009, 12 pp.
International Search Report and Written Opinion of international application No. PCT/US2008/073334, mailed Jan. 12, 2009, 11 pp.
International Search Report and Written Opinion of international application No. PCT/US2008/073369, mailed Nov. 12, 2008, 12 pp.
International Search Report and Written Opinion issued in PCT/US11/46809, mailed Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, 1/4-inch VGA NTSC/PAL CMOS Digital Image Sensor, 98 pp.

(56) References Cited

OTHER PUBLICATIONS

Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Fraulob et al., "Miniature assistance module for robot-assisted heart surgery," Biomed. Tech. 2002, 47 Suppl. 1, Pt. 1: 12-15.
Guber et al., "Miniaturized Instrument Systems for Minimally Invasive Diagnosis and Therapy," Biomedizinische Technic. 2002, Band 47, Erganmngsband 1: 198-201.
Guo et al., "Fish-like Underwater Microrobot with 3 DOF," Proceedings of the 2002 IEEE International Conference on Robotics & Automation, May 2002: 738-743.
Fukuda et al., "Mechanism and Swimming Experiment of Micro Mobile Robot in Water," Proceedings of the 1994 IEEE International Conference on Robotics and Automation, 1994: 814-819.
Guo et al., "Micro Active Guide Wire Catheter System—Characteristic Evaluation, Electrical Model and Operability Evaluation of Micro Active Catheter," Proceedings of the 1996 IEEE International Conference on Robotics and Automation, Apr. 1996: 2226-2231.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committee," U.S. Food and Drug Administration, available at http://www.fda.gov, Finalized: Nov. 7, 2003; Updated: Jun. 24, 2005, 11 pp.
Glukhovsky et al., "The development and application of wireless capsule endoscopy," Int. J. Med. Robot. Comput. Assist. Surgery, 2004; I (1): 114-123.
Hanly et al., "Value of the SAGES Learning Center in introducing new technology," Surgical Endoscopy, 2004; 19(4): 477-483.
Heikkinen et al., "Comparison of laparoscopic and open Nissen fundoplication two years after operation: A prospective randomized trial," Surgical Endoscopy, 2000; 14: 1019-1023.
Horgan et al., "Technical Report: Robots in Laparoscopic Surgery," Journal of Laparoendoscopic & Advanced Surgical Techniques, 2001; 11(6): 415-419.
Menciassi et al., "Robotic Solutions and Mechanisms for a Semi-Autonomous Endoscope," Proceedings of the 2002 IEEE/RSJ Intl. Conference on Intelligent Robots and Svstems, Oct. 2002; 1379-1384.
Micron, http://www.micron.com, 2006, I/4-inch VGA NTSC/PAL CMOS Digital Image Sensor, 98 pp.
Hissink, "Olympus Medical develops capsule camera technology," Dec. 2004, accessed Aug. 29, 2007, http://www.letsgodigital.org , 3 pp.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.
Rentschler et al., "Mechanical Design of Robotic in Vivo Wheeled Mobility," ASME Journal of Mechanical Design, 2006a, pp, I-II.
Rosen et al., "Spherical Mechanism Analysis of a Surgical Robot for Minimally Invasive Surgery—Analytical and Experimental Approaches," Studies in Health Technology and Infonnatics—Medicine Meets Virtual Reality, pp. 442-448, Jan. 2005.
Rosen et al., "Objective Laparoscopic Skills Assessments of Surgical Residents Using Hidden Markov Models Based on Haptic Information and Tool/Tissue Interactions," Studies in Health Technology and Infonnatics—Medicine Meets Virtual Reality, Jan. 2001, 7 pp.
Stiff et al., "Long-term Pain: Less Common After Laparoscopic than Open Cholecystectomy," British Journal of Surgery, 1994; 81: 1368-1370.
Way et al (editors), "Fundamentals of Laparoscopic Surgery," Churchill Livingstone Inc., 1995, 14 pp.
Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.
Dakin et al., "Comparison of laparoscopic skills performance between standard instruments and two surgical robotic systems," Surg Endosc., 2003; 17: 574-579.
Bauer et al., "Case Report: Remote Percutaneous Renal Access Using a New Automated Telesurgical Robotic System," Telemedicine Journal and e-Health 2001; (4): 341-347.
Breedveld et al., "Design of Steerable Endoscopes to Improve the Visual Perception of Depth During Laparoscopic Surgery," ASME, Jan. 2004; vol. 126, pp. 1-5.
Fireman et al., "Diagnosing small bowel Crohn's disease with wireless capsule endoscopy," Gut 2003; 52: 390-392.
Grady, "Doctors Try New Surgery for Gallbladder Removal," The New York Times, Apr. 20, 2007, 3 pp.
Ruurda et al, "Robot-Assisted surgical systems: a new era in laparoscopic surgery," Ann R. Coll Surg Engl., 2002; 84: 223-226.
Fearing et al., "Wing Transmission for a Micromechanical Flying Insect," Proceedings of the 2000 IEEE International Conference on Robotics & Automation, Apr. 2000; 1509-1516.
Worn et al., "Espirit Project No. 33915: Miniaturised Robot for Micro Manipulation (MINIMAN)", Nov. 1998; http://www.ipr.ira.ujka.de/microbot/miniman.
Breda et al., "Future developments and perspectives in laparoscopy," Eur. Urology 2001; 40(1): 84-91.
Allendorf et al., "Postoperative Immune Function Varies Inversely with the Degree of Surgical Trauma in a Murine Model," Surgical Endoscopy 1997; 11: 427-430.
Ang, "Active Tremor Compensation in Handheld Instrument for Microsurgery," Doctoral dissertation, tech report CMU-RI-TR-04-28, Robotics Institute, Carnegie Mellon University, May 2004, 167 pp.
Atmel 80C5X2 Core, http://www.atmel.com, 2006, 186 pp.
Bailey et al., "Complications of Laparoscopic Surgery," Quality Medical Publishers, Inc., 1995, 25 pp.

(56) References Cited

OTHER PUBLICATIONS

Ballantyne, "Robotic Surgery, Telerobotic Surgery, Telepresence, and Telementoring," Surgical Endoscopy, 2002; 16: 1389-1402.
Begos et al., "Laparoscopic Cholecystectomy: From Gimmick to Gold Standard," J Clin Gastroenterol, 1994; I9(4): 325-330.
Berg et al., "Surgery with Cooperative Robots," Medicine Meets Virtual Reality, Feb. 2007, 1 pg.
Breedveld et al., "Locomotion through the Intestine by means of Rolling Stents," Proceedings of the ASME Design Engineering Technical Conferences, 2004, pp. 1-7.
Calafiore et al., "Multiple Arterial Conduits Without Cardiopulmonary Bypass: Early Angiographic Results," Ann Thorac Surg, 1999; 67: 450-456.
Camarillo et al., "Robotic Technology in Surgery: Past, Present, and Future," The American Journal of Surgery, 2004; 188: 2S-15.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Cavusoglu et al., "Telesurgery and Surgical Simulation: Haptic Interfaces to Real and Virtual Surgical Environments," In McLaughlin, M. L., Hespanha, J. P., and Sukhatme, G., editors. Touch in virtual environments, IMSC Series in Multimedia 2001, 28 pp.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4 pp.
CrystalEyes, http://www.reald.com, 2007 (Stere03D visualization for CAVEs, theaters and immersive environments), I pg.
Cuschieri, "Technology for Minimal Access Surgery," BMJ, 1999, 319: 1-6.
Dumpert et al., "Stereoscopic in Vivo Surgical Robots," IEEE Sensors Special Issue on in Vivo Sensors for Medicine, Jan. 2007, 10 pp.
Dumpert et al., "Improving in Vivo Robot Vision Quality," from the Proceedings of Medicine Meets Virtual Reality, Long Beach, CA, Jan. 26-29, 2005, 1 pg.
Faraz et al., "Engineering Approaches to Mechanical and Robotic Design for Minimally Invasive Surgery (MIS)," Kluwer Academic Publishers (Boston), 2000, 13 pp.
Flynn et al, "Tomorrow's surgery: micromotors and microrobots for minimally invasive procedures," Minimally Invasive Surgery & Allied Technologies, 1998; 7(4): 343-352.
Franklin et al., "Prospective Comparison of Open vs. Laparoscopic Colon Surgery for Carcinoma: Five-Year Results," Dis Colon Rectum, 1996; 39: S35-S46.
Fukuda et al., "Micro Active Catheter System with Multi Degrees of Freedom," Proceedings of the IEEE International Conference on Robotics and Automation, May, 1994, pp. 2290-2295.
Falcone et al., "Robotic Surgery," Clin. Obstet. Gynecol. 2003, 46(1): 37-43.
Wolfe et al, "Endoscopic Cholecystectomy: An analysis of Complications," Arch. Surg. Oct. 1991; 126: 1192-1196.
Tendick et al. (1993), "Sensing and Manipulation Problems in Endoscopic Surgery: Experiment, Analysis, and Observation," Presence 2( 1): 66-81.
Chanthasopeephan et al. (2003), "Measuring Forces in Liver Cutting: New Equipment and Experimental Results," Annals of Biomedical Engineering 31: 1372-1382.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Franzino, "The Laprotek Surgical System and the Next Generation of Robotics," Surg Clin North Am, 2003 83(6): 1317-1320.
Smart Pill "Fastastic Voyage: Smart Pill to Expand Testing," http://www.smartpilldiagnostics.com, Apr. 13, 2005, 1 pg.
International Search Report and Written Opinion from international application No. PCT/US2008/073369, mailed Nov. 12, 2008, 12 pp.
U.S. Appl. No. 11/947,097, filed Nov. 29, 2007.
U.S. Appl. No. 12/192,663, filed Aug. 15, 2008.

Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 80C5X2 Core, http://www.atmel.com, 2006, 186pp.
Bailey et al., "Complications of Laparoscopic Surgery," Quality Medical Publishers, Inc., 1995, 25pp.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al, "Telesurgery and Surgical Simulation: Haptic Interlaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al, "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Dumpert et al., "Improving in Vivo Robot Visioin Quality," from the Proceedings of Medicine Meets Virtual Realtiy, Long Beach, CA, Jan. 26-29, 2005. 1 pg.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franzino, "The Laprotek Surgical System and the Next Generation of Robotics," Surg Clin North Am, 2003 83(6).
Fraulob et al., "Miniature assistance module for robot-assisted heart surgery," Biomed. Tech. 2002, 47 Suppl. 1, Pt. 1:12-15.
Fukuda et al, "Mechanism and Swimming Experiment of Micro Mobile Robot in Water," Proceedings of the 1994 IEEE International Conference on Robotics and Automation, 1994: 814-819.

(56) References Cited

OTHER PUBLICATIONS

Fukuda et al, "Micro Active Catheter System with Multi Degrees of Freedom," Proceedings of the IEEE International Conference on Robotics and Automation, May 1994, pp. 2290-2295.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.

Guber et al., "Miniaturized Instrumetn Systems for Minimally Invasive Diagnosis and Therapy," Biomedizinishe Technic. 2002, Band 47, Erganmngsband 1.

International Search Report and Written Opinion issued in PCT/US2008/069822, mailed Aug. 5, 2009, 10 pages.

U.S. Appl. No. 12/324,364, filed Nov. 26, 2008.

Applicant Response to Office Action dated Aug. 21, 2006, in related case U.S. Appl. No. 11/403,756, filed Nov. 21, 2006, 52 pp.

Applicant Response to Office Action dated Aug. 18, 2006, in related case U.S. Appl. No. 11/398,174, filed Nov. 7, 2006, 8 pp.

Examiner Interview Summary dated Nov. 30, 2006, in related case U.S. Appl. No. 11/398,174, 2 pp.

Applicant Response to Office Action dated Oct. 29, 2007, in related case U.S. Appl. No. 11/695,944, filed Jan. 22, 2008, 6 pp.

Applicant Amendment after Notice of Allowance under Rule 312, filed Aug. 25, 2008, in related case U.S. Appl. No. 11/695,944, 6 pp.

Midday, Jeff et al., "Material Handling System for Robotic natural Orifice Surgery", Proceedings of the 2011 Design of medical Devices Conference, Apr. 12-14, 2011, Minneapolis, MN, 4 pages.

Palm, William, "Rapid Prototyping Primer" May 1998 (revised Jul. 30, 2002) (http://www.me.psu.edu/lamancusa/rapidpro/primer/chapter2.htm).

* cited by examiner

MODULAR AND COOPERATIVE MEDICAL DEVICES AND RELATED SYSTEMS AND METHODS

CROSS-REFERENCE TO RELATED APPLICATIONS

This application claims priority to Provisional Application No. 60/956,032, filed Aug. 15, 2007; Provisional Application No. 60/990,076, filed Nov. 26, 2007; Provisional Application No. 60/990,106, filed Nov. 26, 2007; Provisional Application No. 61/025,346, filed Feb. 1, 2008; and Provisional Application No. 61/030,617, filed Feb. 22, 2008, all of which are hereby incorporated herein by reference in their entireties.

GOVERNMENT SUPPORT

This invention was made with government support under Grant No. R21EB5663-2, awarded by the National Institute of Biomedical Imaging and Bioengineering within the National Institutes of Health. Accordingly, the government has certain rights in the invention.

TECHNICAL FIELD

The embodiments disclosed herein relate to various medical devices and related components, including robotic and/or in vivo medical devices and related components. Certain embodiments include various modular medical devices, including modular in vivo and/or robotic devices. Other embodiments relate to modular medical devices in which the various modular components are segmented components or components that are coupled to each other. Further embodiment relate to methods of operating the above devices, including methods of using various of the devices cooperatively.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

SUMMARY

One embodiment disclosed herein relates to a modular medical device or system having at least one modular component configured to be disposed inside a cavity of a patient. The modular component has a body, an operational component, and a coupling component. In a further embodiment, the modular component can be coupled at the coupling component to a second modular component. In a further alternative, a third modular component can be coupled to the first and second modular components.

Another embodiment disclosed herein relates to a modular medical device or system having a body configured to be disposed inside a cavity of a patient. The device also has at least a first modular component coupleable to the body, the first modular component having a first operational component. In another embodiment, the device also as a second modular component coupleable to the body, the second modular component having a second operational component. In further alternatives, the device can also have third and fourth modular components or more.

Yet another embodiment disclosed herein relates to a modular medical device or system having a first modular component, a second modular component, and a third modular component. In one embodiment, the three modular components are pivotally connected to each other in a triangular configuration. In this embodiment, the first and third components can be coupled together at a releasable mating connection. According to one embodiment, each of the modular components has an inner body and an outer body, wherein the inner body is rotatable in relation to the outer body. In addition, each modular component has an operational component associated with the inner body. In accordance with another implementation, each of the inner and outer bodies comprise an opening, and each of the inner bodies is rotatable to position the inner and outer openings in communication, whereby the operational components are accessible. In a further alternative, each pivotal connection of the device or system has a mechanism configured to urge the mating or coupling connections at the ends of the first and third components into contact. Alternatively, the device has four modular components that are pivotally connected to each other in a quadrangular configuration. In further alternatives, additional modular components can be pivotally connected to each other.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
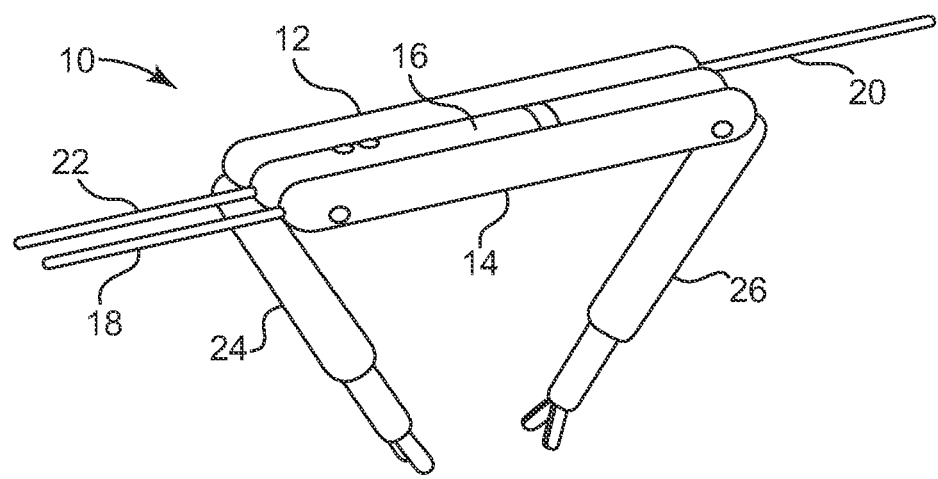
FIG. 1A is a perspective view of a modular medical device, according to one embodiment.

The various systems and devices disclosed herein relate to devices for use in medical procedures and systems. More specifically, various embodiments relate to various modular or combination medical devices, including modular in vivo and robotic devices and related methods and systems, while other embodiments relate to various cooperative medical devices, including cooperative in vivo and robotic devices and related methods and systems.

It is understood that the various embodiments of modular and cooperative devices and related methods and systems disclosed herein can be incorporated into or used with any other known medical devices, systems, and methods.

For example, the various embodiments disclosed herein can be incorporated into or used with any of the medical devices and systems disclosed in copending U.S. application Ser. No. 11/932,441 (filed on Oct. 31, 2007 and entitled "Robot for Surgical Applications"), Ser. No. 11/695,944 (filed on Apr. 3, 2007 and entitled "Robot for Surgical Applications"), Ser. No. 11/947,097 (filed on Nov. 27, 2007 and entitled "Robotic Devices with Agent Delivery Components and Related Methods), Ser. No. 11/932,516 (filed on Oct. 31, 2007 and entitled "Robot for Surgical Applications"), Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), Ser. No. 12/171,413 (filed on Jul. 11, 2008 and entitled "Methods and Systems of Actuation in Robotic Devices"), 60/956,032 (filed on Aug. 15, 2007), 60/983,445 (filed on Oct. 29, 2007), 60/990,062 (filed on Nov. 26, 2007), 60/990,076 (filed on Nov. 26, 2007), 60/990,086 (filed on Nov. 26, 2007), 60/990, 106 (filed on Nov. 26, 2007), 60/990,470 (filed on Nov. 27, 2007), 61/025,346 (filed on Feb. 1, 2008), 61/030,588 (filed on Feb. 22, 2008), and 61/030,617 (filed on Feb. 22, 2008), all of which are hereby incorporated herein by reference in their entireties.

Certain device implementations disclosed in the applications listed above can be positioned within a body cavity of a patient, including certain devices that can be positioned against or substantially adjacent to an interior cavity wall, and related systems. An "in vivo device" as used herein means any device that can be positioned, operated, or controlled at least in part by a user while being positioned within a body cavity of a patient, including any device that is positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain implementations disclosed herein relate to modular medical devices that can be assembled in a variety of configurations.

Figure 1B:
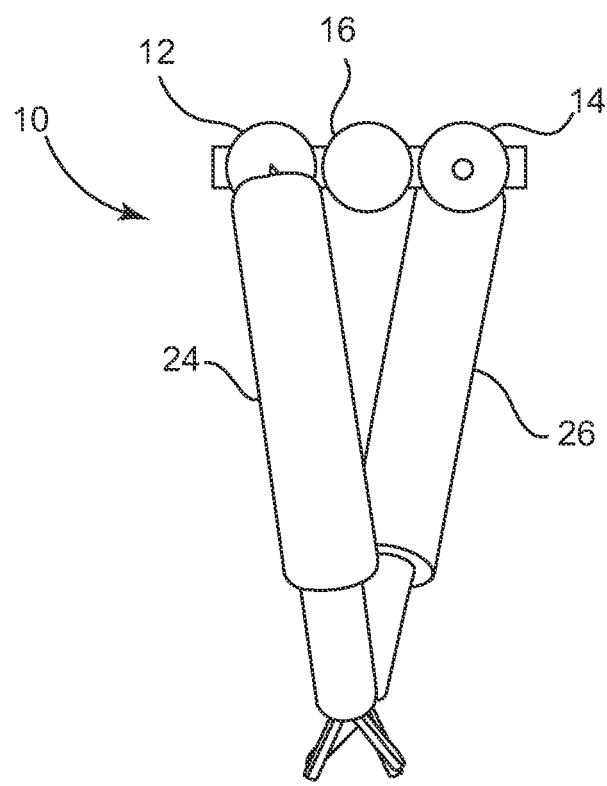
FIG. 1B is a side view of the modular medical device of FIG. 1A.
Figure 1C:
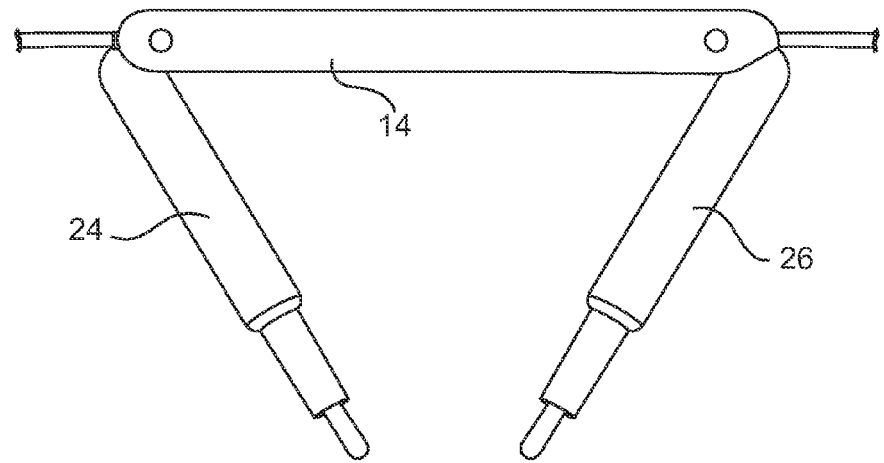
FIG. 1C is a front view of the modular medical device of FIG. 1A.

FIGS. 1A-1C depict an exemplary "combination" or "modular" medical device 10, according to one embodiment. For purposes of this application, both "combination device" and "modular device" shall mean any medical device having modular or interchangeable components that can be arranged in a variety of different configurations. The combination device 10 shown in FIGS. 1A-1C has three modular components 12, 14, 16 coupled or attached to each other. More specifically, the device 10 has two robotic arm modular components 12, 14 and one robotic camera modular component 16 disposed between the other two components 12, 14. In this implementation, the modular component 16 contains an imaging component (not shown) and one or more lighting components (not shown), while each of the other modular components 12, 14 have an arm 24, 26 respectively and do not contain any lighting or imaging components. That is, in this embodiment, the modular component 16 is a modular imaging and lighting component 16 while the two modular components 12, 14 are modular arm components 12, 14. In the resulting configuration, the components 12, 14, 16 are coupled or attached to each such that the camera component 16 is disposed between the two modular arm components 12, 14. As will be discussed in further detail below, this configuration of the components 12, 14, 16 is merely one of several possible configurations of such modular components.

In accordance with one embodiment, the strategic positioning of various operational components in the combination device 10 in FIGS. 1A-1C results in an optimization of the volume in each of the individual components 12, 14, 16. That is, the space in modular components 12, 14 that would have been required for an imaging component and/or a lighting component is instead utilized for larger and/or more complex actuators or other components. If larger or more complex actuators are utilized in both modular components 12, 14, greater force can be applied to each arm 24, 26, thereby making it possible for the combination device 10 to perform additional procedures that require greater force.

In comparison to the space optimization advantage of the combination device 10, a non-combination device must have all the necessary components such as imaging and illumination components in the device body along with the actuators, thereby reducing the space available and requiring that the actuators and other components be small enough such that they all fit in the device together.

According to one alternative embodiment, the additional space available in the combination device 10 created by the space optimization described above could be used to provide for more sophisticated components such as more complex camera focusing mechanisms or mechanisms to provide zoom capabilities. In a further alternative, the various components could be distributed across the modular components 12, 14, 16 of the combination device 10 in any fashion. For example, the illumination and imaging components could be both positioned in either modular component 12 or 14. Alternatively, one of the illumination and imaging components could be disposed in any one of the three modular components 12, 14, 16 and the other component could be disposed in one of the other three components 12, 14, 16. It is understood that any possible combination of various components such as illumination, actuation, imaging, and any other known components for a medical device can be distributed in any combination across the modular components of any combination device.

Another advantage of the combination devices such as that shown in FIGS. 1A-1C, according to one implementation, is the capacity to increase the number of a particular type of component in the device. For example, one embodiment of a combination device similar to the device 10 in FIGS. 1A-1C could have lighting components on more than one of the modular components 12, 14, 16, and further could have more than one lighting component on any giving modular component. Thus, the combination device could have a number of lighting components ranging from one to any number of lighting components that could reasonably be included on the device. The same is true for any other component that can be included in two or more of the modular components.

In accordance with a further embodiment, another possible advantage of the various combination device embodiments disclosed herein relates to the fact that the various separable modular components (instead of one larger device) simplifies insertion because each component separately is shorter and less complex. Thus, each component individually has a smaller cross-section and can be inserted into a body cavity through a smaller incision, port, or any other known delivery device than the larger, non-combination device.

It is understood that, according to various embodiments, a combination device such as the device 10 depicted in FIGS. 1A-1C could have additional modular components coupled thereto. Thus, the device could have additional arms or other modular components such as, for example, one or more of a sensing modular component, an illumination modular component, and/or a suction/irrigation modular component.

In use, modular components (such as, for example, components 12, 14, 16 of FIGS. 1A, 1B, and 1C) are each separately inserted into the target cavity of a patient. Typically, each of the components are inserted through a laparoscopic port, an incision, or a natural orifice. Alternatively, the components are inserted by any known method, procedure, or device. Once each of the desired components (which could range from one to several components) is positioned in the target cavity, the components can be assembled into a combination device such as, for example, the combination device 10 depicted in FIGS. 1A-1C, by coupling the components together in a desired configuration. After the procedure has been performed, the components of the combination device can be decoupled and each separately removed. Alternatively, once a portion of a procedure is performed, one or more of the components can be decoupled and removed from the cavity and one or more additional components can be inserted into the cavity and coupled to the combination device for one or more additional procedures for which the component replacement was necessary.

The various modular component embodiments disclosed herein can be coupled to create a combination device in a variety of ways. To configure the combination device 10 as shown in FIG. 1A, the exemplary modular components 12, 14, 16 each have four mating or coupling components as best shown in FIGS. 2A, 2B, and 3.

Figure 2A:
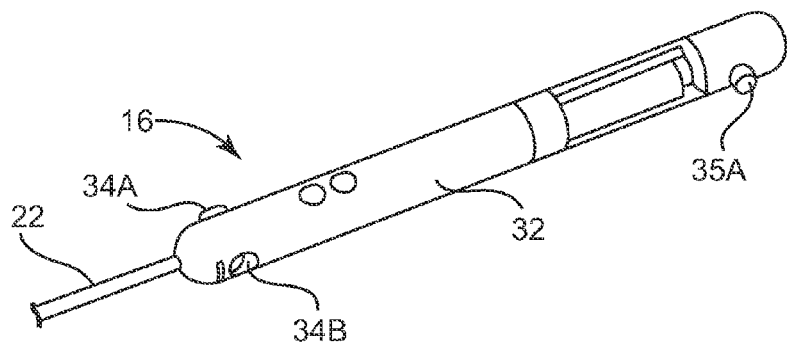
FIG. 2A depicts a perspective view of a modular component, according to one embodiment.
Figure 2B:
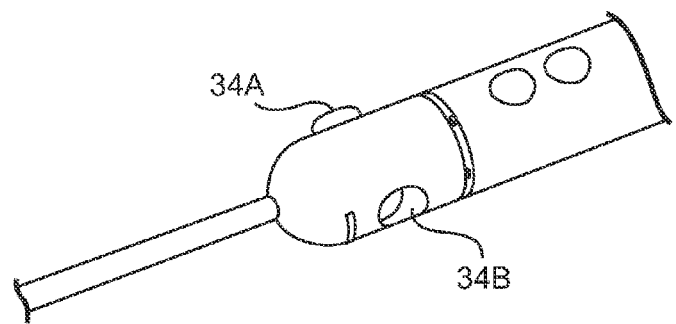
FIG. 2B depicts a close-up perspective view of a portion of the modular component of FIG. 2A.
Figure 3:
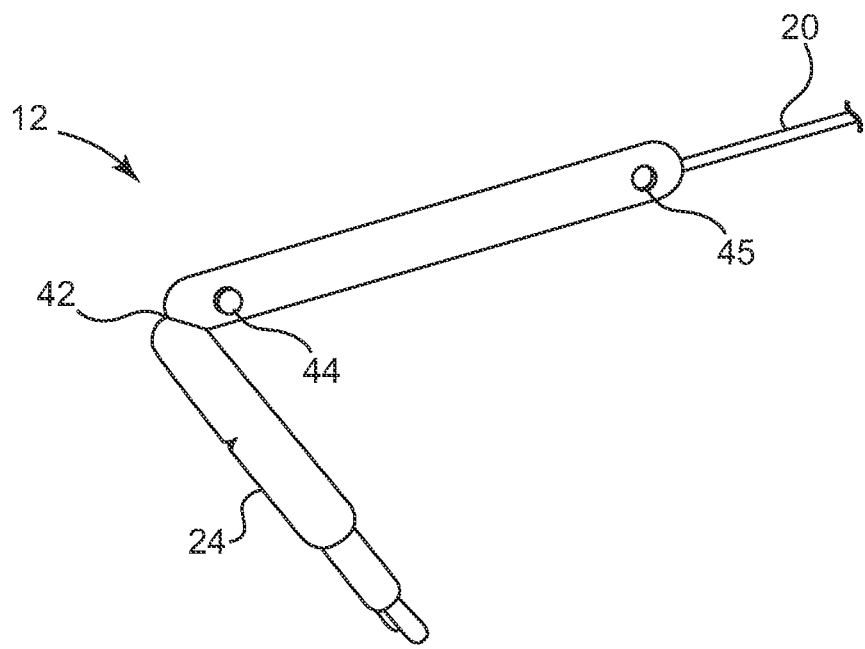
FIG. 3 is a perspective view of another modular component, according to another embodiment.

In FIGS. 2A and 2B, the modular component 16 provides one example of an attachment mechanism for coupling modular components together. That is, the device 16 has four mating or coupling components 34A, 34B, 35A, (and 35B, which is not shown) for coupling to other devices or modular components. In this embodiment as best shown in FIG. 2A, there are two coupling components 34, 35 at each end of the device 30, with two components 34A, 34B at one end and two more at the other end (depicted as 35A and another such component on the opposite side of the component 16 that is not visible in the figure). Alternatively, the modular component 16 can have one coupling component, two coupling components, or more than two coupling components.

To better understand the coupling components of this embodiment, FIG. 2B provides an enlarged view of one end of the device 16, depicting the male coupling component 34A and female coupling component 34B. The male component 34A in this embodiment is configured to be coupleable with a corresponding female component on any corresponding modular component, while the female component 34B is configured to be coupleable with a corresponding male component on any corresponding modular component.

It is understood that the mechanical male/female coupling components discussed above are merely exemplary coupling mechanisms. Alternatively, the components can be any known mechanical coupling components. In a further alternative, the coupling components can also be magnets that can magnetically couple with other magnetic coupling components in other modular components. In a further embodiment, the coupling components can be a combination of magnets to help with initial positioning and mechanical coupling components to more permanently couple the two modules.

Returning to the embodiment depicted in FIG. 1A, two modular components 12, 14, each having an arm 24, 26 (respectively), are coupled to the modular component 16. FIG. 3 depicts component 12, but it is understood that the following discussion relating to modular component 12 applies equally to component 14. Modular component 12 as shown in FIG. 3 has male/female coupling components 44, 45 that can be coupled to component 16 as discussed above. Alternatively, as discussed above, any known coupling components can be incorporated into this component 12 for coupling with other modular components.

According to one implementation, the arm 24 in the embodiment of FIG. 3 provides the four degrees of freedom ("DOF"). These four degrees of freedom include three rotations and one extension. Two rotations occur about the joint 42. The third rotation occurs along the axis of the arm 24. The extension also occurs along the axis of the arm 24. Alternatively, any known arm implementation for use in a medical device can be used.

Figure 4:
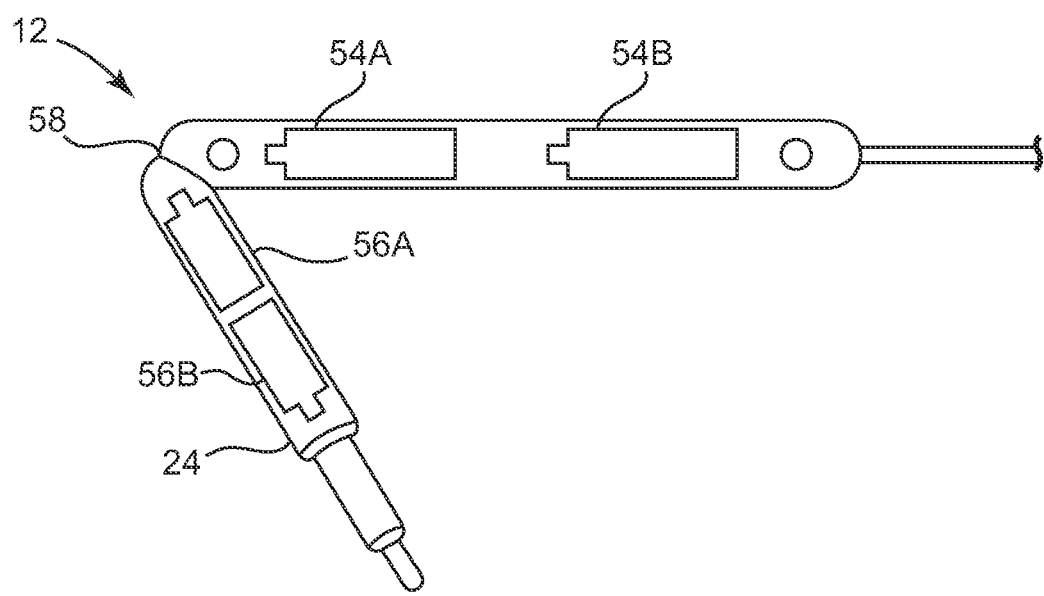
FIG. 4 is a front cutaway view of another modular component, according to a further embodiment.

FIG. 4 depicts an alternative exemplary embodiment of modular component 12. In this implementation, the actuator components 54A, 54B, 56A, 56B are depicted in the component 12. That is, two actuators 54A, 54B are provided in the body of the device 12, while two additional actuators 56A, 56B are provided in the arm 24. According to one embodiment, actuators 54A, 54B are configured to actuate movement of the arm 24 at the shoulder joint 58, while actuators 56A, 56B are configured to actuate movement at the arm 24. Alternatively, it is understood that any configuration of one or more actuators can be incorporated into a modular component to actuate one or more portions of the component or device.

In accordance with further implementations, it is understood that the various modular components discussed herein can contain any known operational components contained in any non-modular medical device. For example, the modular component 16 has a camera 32 and further can have all of the associated components and/or features of the modular components or medical devices discussed above, including the medical devices and components disclosed in the applications incorporated above.

Figure 5A:
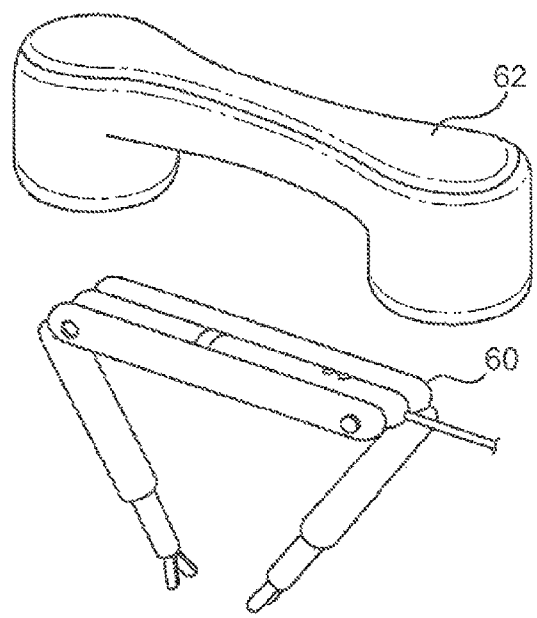
FIG. 5A is a perspective view of a modular medical device control system, according to one embodiment.
Figure 5B:
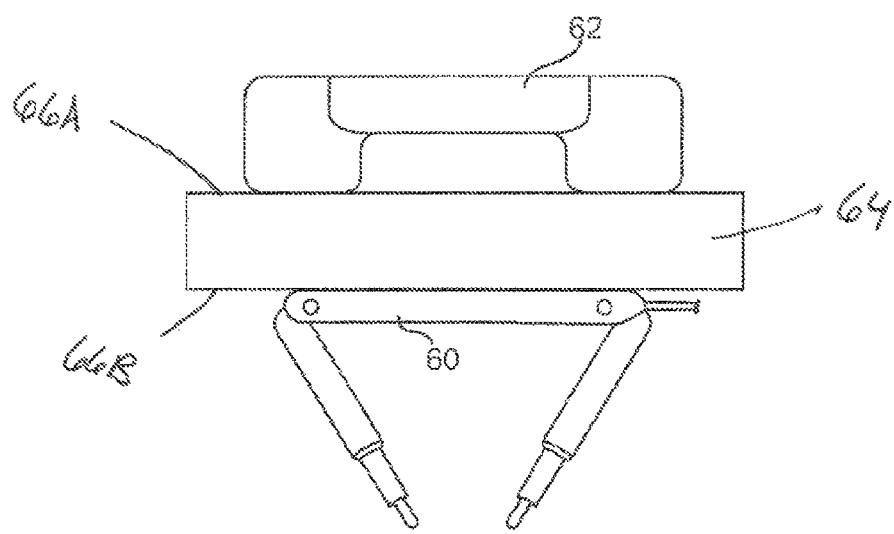
FIG. 5B is a front cutaway view of the system of FIG. 5A.

In use, the various modular components and combination devices disclosed herein can be utilized with any known medical device control and/or visualization systems, including those system disclosed in the applications incorporated above. These modular components and combination devices can be utilized and operated in a fashion similar to any medical devices disclosed in those applications. For example, as shown in FIGS. 5A and 5B, a combination device or modular component 60 can be utilized with an external magnetic controller 62. In this embodiment, the device 60 has magnetic components (not shown) that allow the device 60 to be in magnetic communication with the external controller 62. It is understood that the device 60 can operate in conjunction the external controller 62 in the same fashion described in the applications incorporated above, such that the external controller 62 is located on an external surface 66A of a patient's cavity wall 64 while the combination device 60 is positioned against the internal surface 66B of the cavity wall 64.

In use, the various modular components and combination devices disclosed herein can be utilized with any known medical device control and/or visualization systems, including those system disclosed in the applications incorporated above. These modular components and combination devices can be utilized and operated in a fashion similar to any medical devices disclosed in those applications. For example, as shown in FIGS. 5A and 5B, a combination device or modular component 60 can be utilized with an external magnetic controller 62. In this embodiment, the device 60 has magnetic components (not shown) that allow the device 60 to be in magnetic communication with the external controller 62. It is understood that the device 60 can operate in conjunction the external controller 62 in the same fashion described in the applications incorporated above.

Figure 6A:
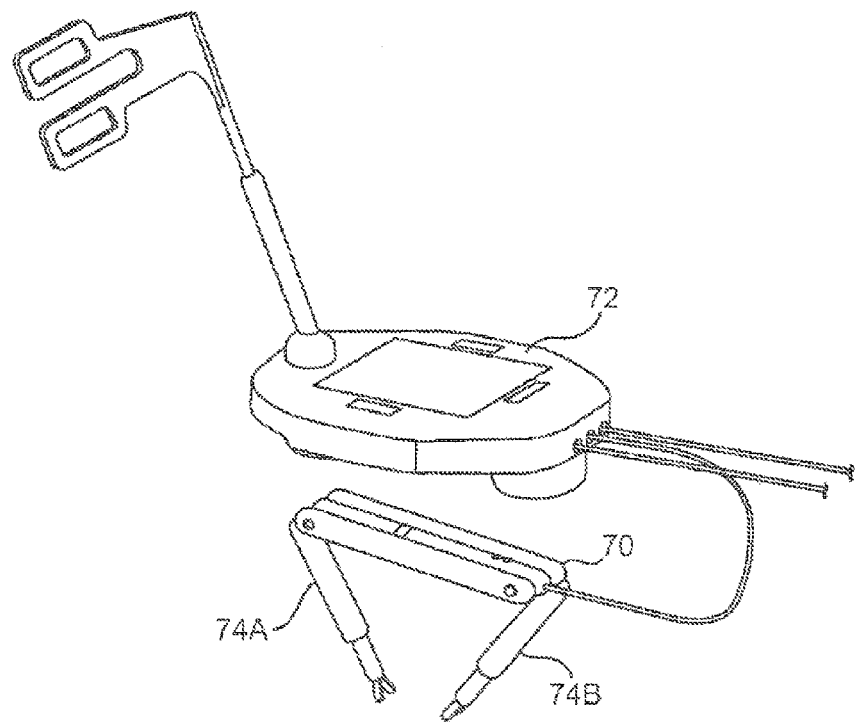
FIG. 6A is a perspective view of a modular medical device control and visualization system, according to one embodiment.
Figure 6B:
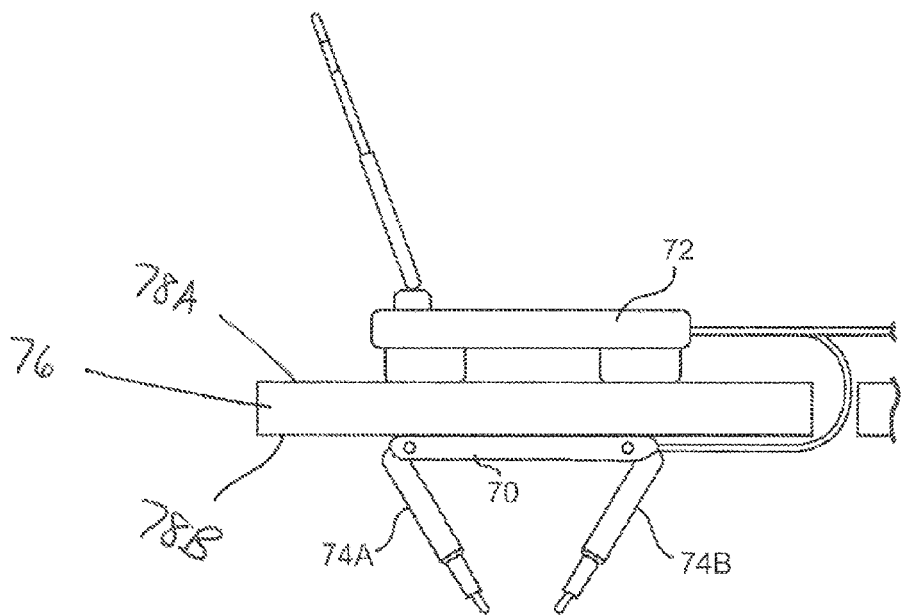
FIG. 6B is a front cutaway view of the system of FIG. 6A.

In another similar example as depicted in FIGS. 6A and 6B, a combination device or modular component 70 can be utilized with an external controller and visualization component 72. In this embodiment, the device 70 has magnetic components (not shown) that allow the device 70 to be in magnetic communication with the external controller 72 and further has arms 74A, 74B that can be operated using the controller 72. It is understood that the device 70 can operate in conjunction the external component 72 in the same fashion described in the applications incorporated above, such that the external controller 72 is located on an external surface 78A of a patient's cavity wall 76 while the combination device 70 is positioned against the internal surface 78B of the cavity wall 76.

In another similar example as depicted in FIGS. 6A and 6B, a combination device or modular component 70 can be utilized with an external controller and visualization component 72. In this embodiment, the device 70 has magnetic components (not shown) that allow the device 70 to be in magnetic communication with the external controller 72 and further has arms 74A, 74B that can be operated using the controller 72. It is understood that the device 70 can operate in conjunction the external component 72 in the same fashion described in the applications incorporated above.

Figure 7A:
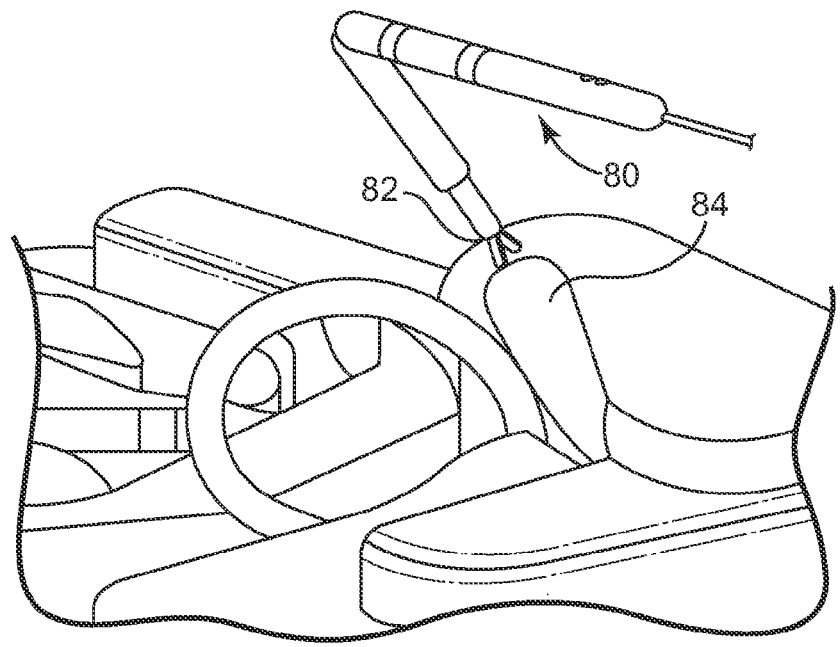
FIG. 7A is a perspective cutaway view of a modular medical device control and visualization system, according to another embodiment.
Figure 7B:
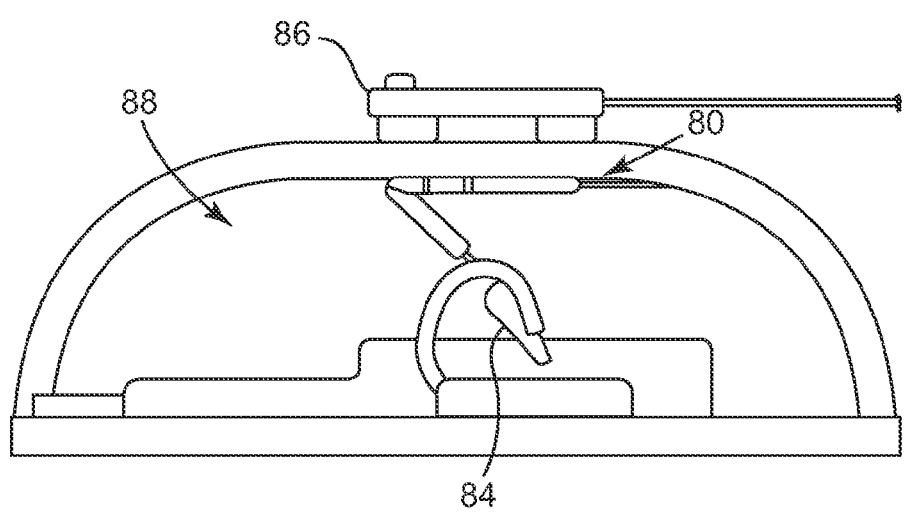
FIG. 7B is a front cutaway view of the system of FIG. 7A.

According to one implementation, a modular device can be used for a variety of surgical procedures and tasks including, but not limited to, tissue biopsy and tissue retraction. For example, as shown in FIGS. 7A and 7B in accordance with one embodiment, a device 80 having a grasper 82 can be used to retract the gall bladder 84 during a cholecystectomy procedure.

Figure 8A:
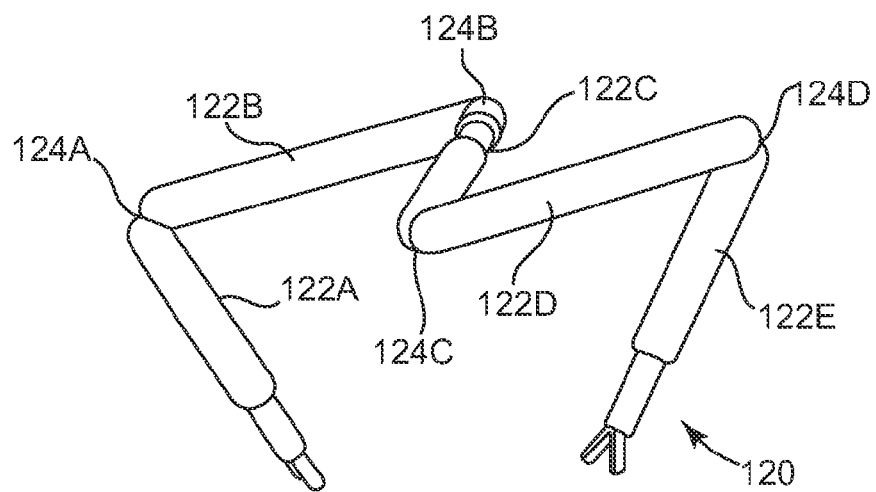
FIG. 8A is a perspective view of a modular medical device, according to another embodiment.
Figure 8B:
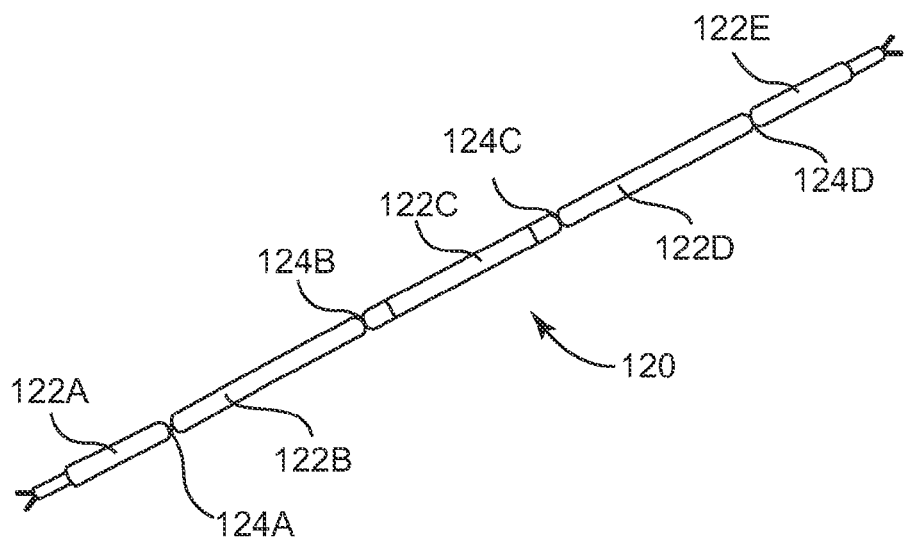
FIG. 8B is another perspective view of the device of FIG. 8A.

In accordance with one alternative, any of the modular components disclosed herein can be assembled into the combination device prior to insertion into the patient's cavity. One exemplary embodiment of such a combination device is set forth in FIGS. 8A and 8B, which depict a combination device 120 having modular components 122A, 122B, 122C, 122D, 122E that are coupled to each other using hinge or rotational joints 124A, 124B, 124C, 124D, 124E (as best shown in FIG. 8B). This device 120 as shown can fold together or otherwise be configured after insertion as shown in FIG. 8A. One advantage of this embodiment, in which the modular components 122A-122E are coupled to each other, is that in vivo assembly of the combination device 120 is simplified.

Figure 9:
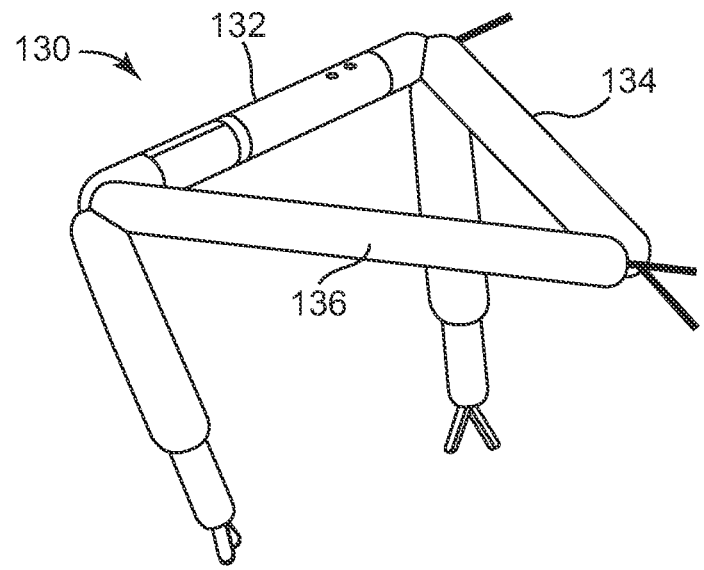
FIG. 9 is a perspective view of another modular medical device, according to a further embodiment.

In a further alternative embodiment as best shown in FIG. 9, any of the modular components disclosed or contemplated herein are inserted separately into the target cavity and subsequently assembled with the modular components being connected end-to-end (in contrast to a side-by-side configuration similar to that depicted in FIGS. 1A-1C). More specifically, the combination device 130 in FIG. 9 has three modular components 132, 134, 136. One of the components is a camera modular component 132, while the other two are robotic arm modular components 134, 136. These three components 132, 136, 136 are connected to form the tripod-like combination device 130 as shown.

Figure 10:
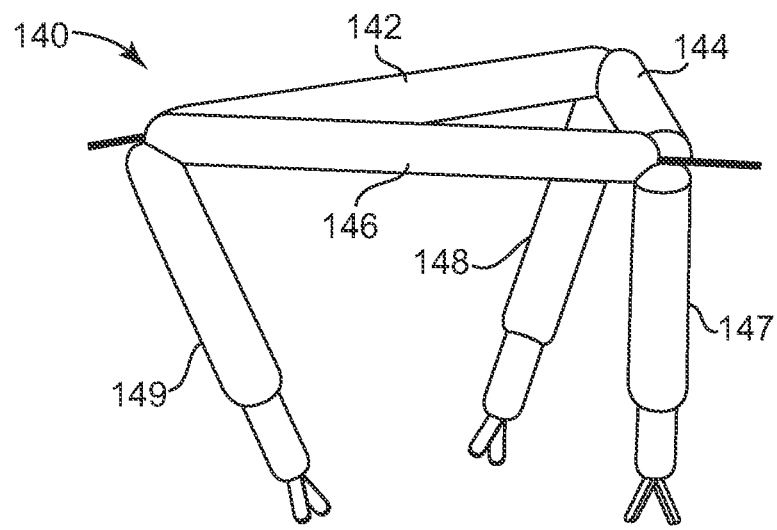
FIG. 10 is a perspective view of a further modular medical device, according to another embodiment.

In yet another implementation, FIG. 10 depicts another combination device 140 having a generally triangular configuration. That is, the device 140 has three arm modular components 142, 144, 146 that are coupled together end-to-end, with each component 142, 144, 146 having an arm 148, 147, 149, respectively. In one embodiment, the three-armed robot could be assembled using three one-arm segments as shown in FIG. 10. Alternatively, the three-armed robot could be assembled by linking three modular bodies end-to-end and coupling an arm component to each linkage of the modular bodies.

Alternatively, additional modular components could be added to a tripod-like combination device such as the devices of FIGS. 9 and 10. For example, one or more additional modular components could be positioned adjacent and parallel to one or more of the three previously-coupled modular components such that one or more side of the three sides have a "stacked" configuration with at least two modular components stacked next to each other.

As mentioned above, according to one embodiment, a particularly useful aspect of using modular medical devices during medical procedures, including modular robotic and/or in vivo devices as described herein, is the ability to insert multiple modular components, such as any of the modular components described or contemplated herein, into a patient's body and subsequently assemble these into a more complex combination device in vivo. In one implementation, more than one modular component is inserted or positioned in the patient's body (through a natural orifice or more conventional methods) and then the components are either surgically assembled or self-assembled once inside the patient's body, in a location such as the peritoneal cavity, for example.

Surgical (or procedural) assembly can involve the surgeon attaching the modular components by using standard laparoscopic or endoscopic tools, or could involve the surgeon using specifically developed tools for this purpose. Alternatively, surgical assembly could instead or further include the surgeon controlling a robotic device disposed within the patient's body or exterior to the body to assemble the modular components. Self assembly, on the other hand, can involve the modular components identifying each other and autonomously assembling themselves. For example, in one embodiment of self assembly, the modular components have infrared transmitters and receivers that allow each component to locate attachment points on other components. In another example, each modular component has a system that utilizes imaging to identify patterns on other modular components to locate attachment points on those other components. In a further alternative, assembly could also include both surgical and self-assembly capabilities.

After the surgical procedure is completed, the components are disassembled and retracted. Alternatively, the robotic device or system can be configurable or reconfigurable in vivo to provide different surgical features during different portions of the procedure. That is, for example, the components of the device or devices can be coupled together in one configuration for one procedure and then disassembled and re-coupled in another configuration for another procedure.

One further exemplary embodiment of a suite of modular components is set forth in FIGS. 11-17. It is understood that such a suite of components can be made available to a surgeon or user, and the surgeon or user can utilize those components she or he desires or needs to create the combination device desired to perform a particular procedure. In one embodiment, since the devices and components are modular, the user (or team) can assemble the procedure-specific robotic device or devices in vivo at the onset of the procedure.

The modular components can include any known procedural or operational component, including any component discussed elsewhere herein (such as those depicted in FIGS. 1A-4, and/or 8A-10) or any component disclosed in the applications incorporated above that can be used as modular component. For example, the various modular components depicted in FIGS. 11-17 include a variety of different operational components or other types of components.

Figure 11:
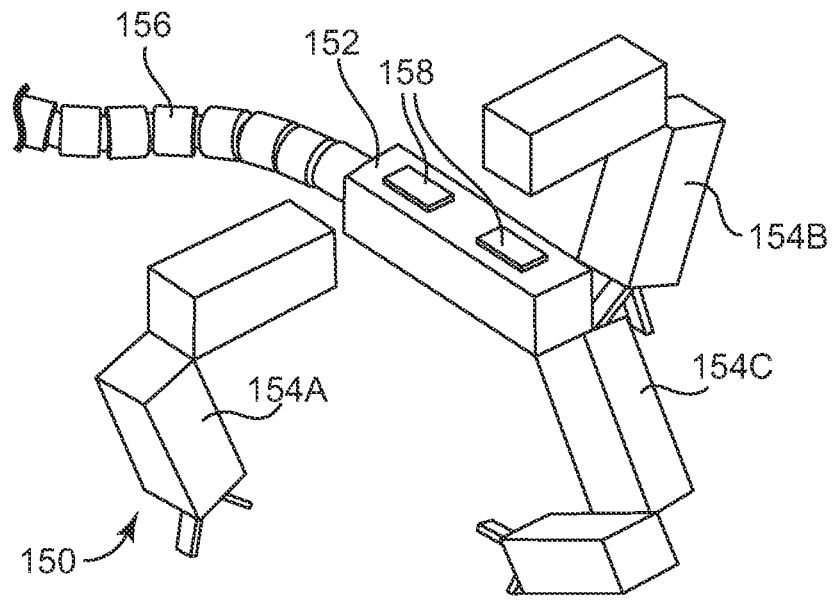
FIG. 11 is a perspective view of another modular medical device, according to one embodiment.
Figure 12A:
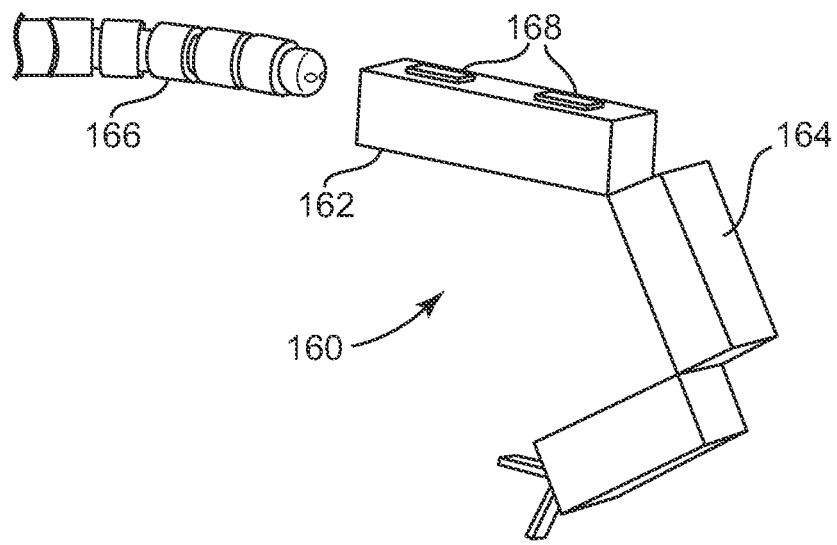
FIG. 12A is a perspective view of another modular medical device, according to a further embodiment.
Figure 12B:
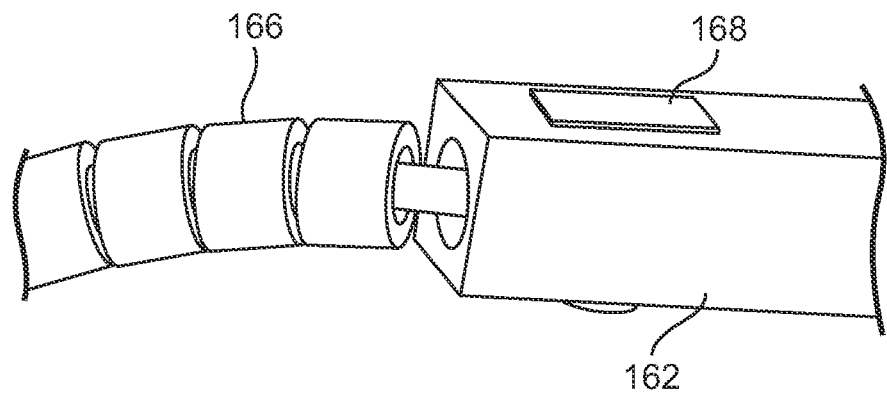
FIG. 12B is a close-up perspective view of a part of the device of FIG. 12A.
Figure 12C:
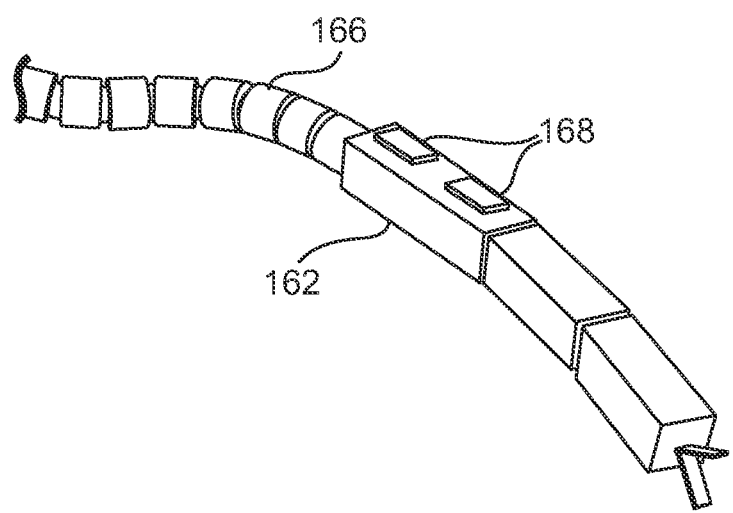
FIG. 12C is another perspective view of the device of FIG. 12A.
Figure 13:
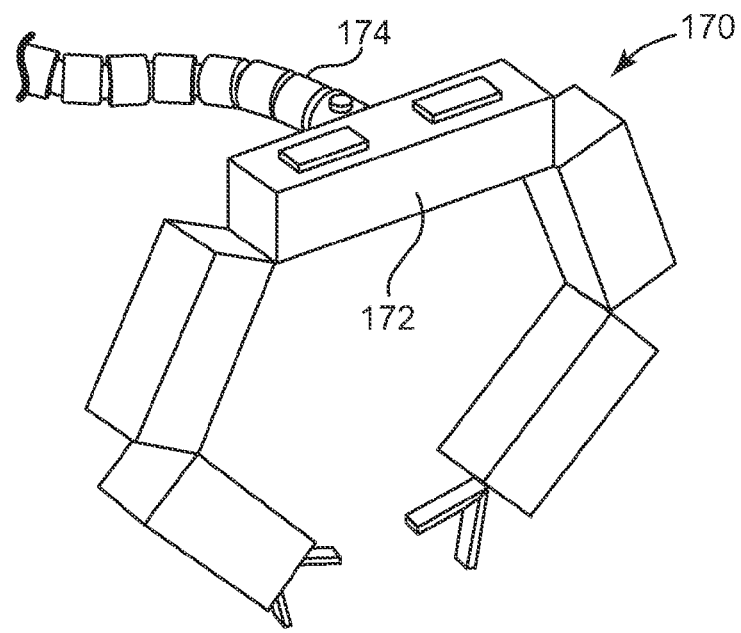
FIG. 13 is a perspective view of a further modular medical device, according to another embodiment.

More specifically, FIGS. 11-13 depict various modular combination device embodiments having a body that is coupled to at least one arm component and a lockable tube. For example, FIG. 11 shows a combination device 150 having a body 152 coupled to three operational arm components 154A, 154B, 154C, and a lockable tube 156. In one aspect, the body 152 can also have at least one magnet 158 (or two magnets as depicted in the figure) that can be used to position the device within the patient's cavity. That is, according to one implementation similar to those described above in relation to other devices, the magnet(s) 158 can be magnetically coupled to an external magnet controller or visualization component to position the device 150.

The lockable tube 156 can be a reversibly lockable tube as disclosed in U.S. application Ser. No. 12/171,413, filed on Jul. 11, 2008, which is incorporated by reference above. The tube 156 and device 150 can be operated in any fashion as described in that application. Alternatively, the tube 156 can be a flexible tube that can be stabilized or held in place using a series of magnets adjacent to or near the flexible tube or a series of needles inserted through the external wall of the patient's body. For example, magnets can be positioned in one or more of the modular components of the flexible tube. In use, one or more magnets are positioned externally with respect to the target cavity in such a fashion as to position the tube and/or robotic device into the desired location.

In use, as also described in the above-incorporate application, a reversibly lockable tube and robotic device (such as, for example, the tube 156 and device 150 depicted in FIG. 11) can be used together to accomplish various tasks. That is, the tube can be operably coupled to the device (as shown in FIG. 11, for example) and contain any required connection components such as connections for hydraulic, pneumatic, drive train, electrical, fiber optic, suction, or irrigation systems, or any other systems or connections that require physical linkages between the device positioned in the patient's body and some external component or device. In one embodiment, the robotic device is first positioned at the desired location in the patient's body and then the tube is inserted and connected to the device. Alternatively, the robotic device can be coupled to the tube prior to insertion, and then both the device and the tube are inserted into the patient's body and the device is then positioned at the desired location.

FIGS. 12A-12C depict another embodiment of a combination device coupled to a lockable tube. More specifically, FIGS. 12A, 12B, and 12C depict a combination device 160 having a body 162 coupled to one operational arm component 164 and a lockable tube 166. As with the device in FIG. 11, the body 162 has two magnets 168 that can be used in conjunction with an external magnet controller to position the device 160 and tube 166 as desired by the user. Alternatively, the body 162 can have one magnet or more than two magnets. In addition, according to one embodiment as best shown in FIG. 12A, the device 160 and the tube 166 can be initially unattached. Prior to use, the body 162 and tube 166 can be coupled as best shown in FIG. 12B. In one embodiment, the body 162 and tube 166 can be coupled prior to insertion or alternatively can be coupled after the device 160 and tube 166 have been positioned in the desired location in the patient's body.

FIG. 13 shows another embodiment of another combination device 170 similar to those depicted in FIGS. 11-12C except that the body 172 is coupled to the tube 174 at a location along the body 172 rather than at an end of the body 172. It is further understood that a tube as disclosed herein can be coupled to any of these combination devices at any point along the body or any of the modular components.

Figure 14:
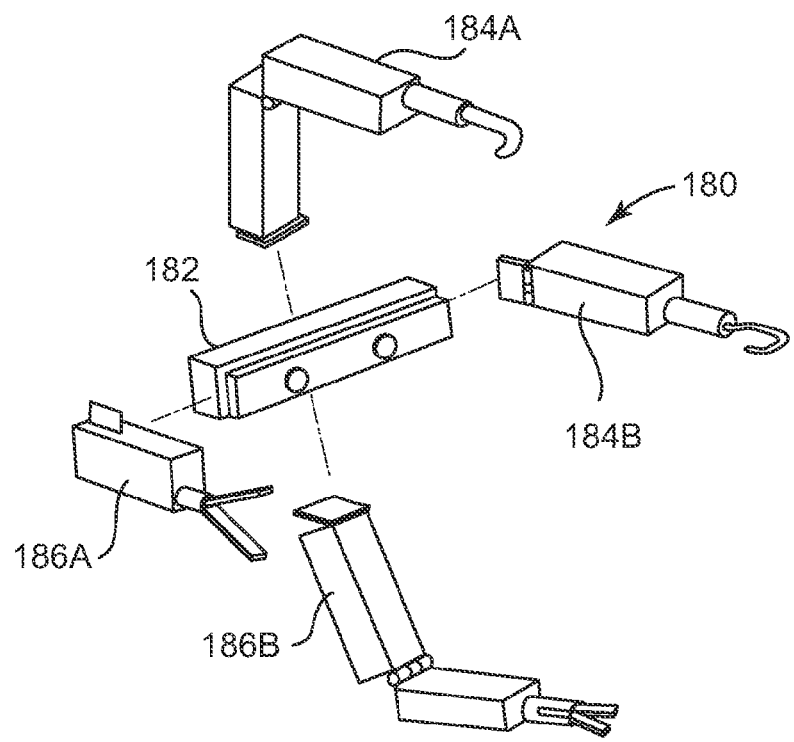
FIG. 14 is a perspective view of the disassembled components of another modular medical device, according to one embodiment.

Another example of a combination device that is made up a suite of modular components is set forth in FIG. 14. The combination device 180 has an imaging modular component 182 (also referred to as a "module"), two cautery arms or modules 184A, 184B, and two grasper arms or modules 186A, 186B. It is understood that the imaging module 182 in this embodiment is the body 182 of the device 180, but could also be an arm in another implementation. It is further understood that the various modules 184, 186 coupled to the device 180 could be configured in any configuration.

Figure 15:
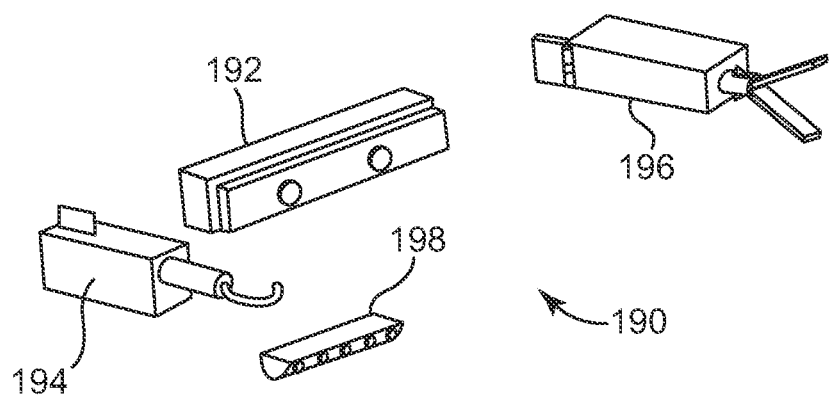
FIG. 15 is a perspective view of the disassembled components of a further modular medical device, according to another embodiment.
Figure 16:
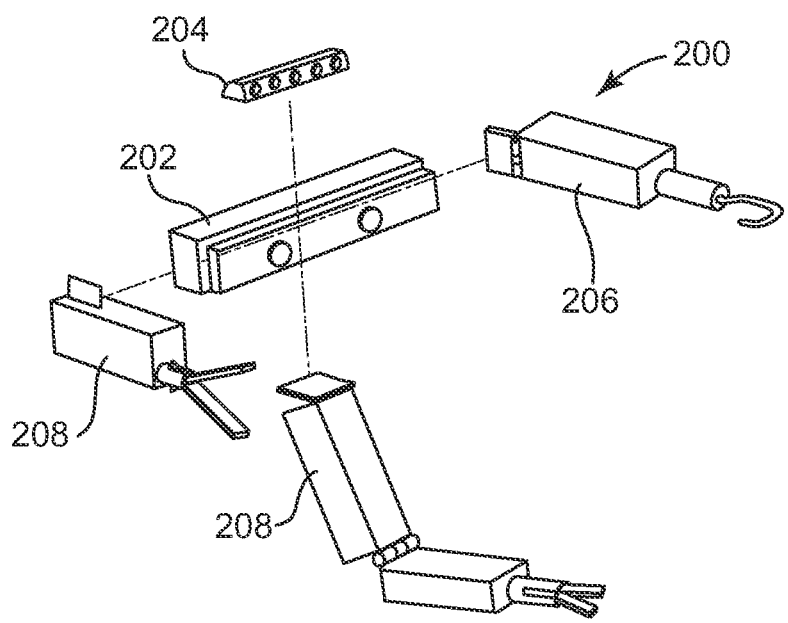
FIG. 16 is a perspective view of the disassembled components of a further modular medical device, according to another embodiment.

An alternative combination device embodiment utilizing various modules from a suite of modular components is depicted in FIG. 15. This device 190 has an imaging module 192, a cautery module 194, a grasper module 196, and a lighting module 198. Similarly, FIG. 16 depicts yet another alternative combination device 200 having an imaging module 202, a lighting module 204, a cautery module 206, and two grasper modules 208.

Figure 17:
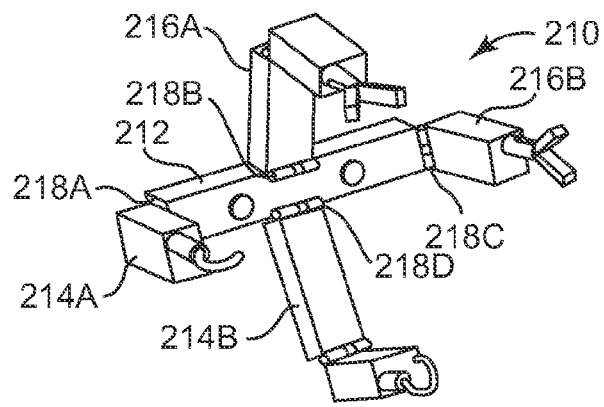
FIG. 17 is a perspective view of an assembled modular medical device, according to a further embodiment.

FIG. 17 depicts a further alternative implementation of a fully assembled combination device 210 having a body 212, two cautery modules 214A, 214B, and two grasper modules 216A, 216B. As shown in the figure, each of the modules is coupled to the body via a hinge coupling 218A, 218B, 218C, 218D. Alternatively, the coupling can be any known coupling, including, for example, a pivotal coupling. In a further alternative, the non-arm modules can be substantially or removably fixed to the body component, such as the lighting module 204 depicted in FIG. 16.

It is understood that any number of additional exemplary modular components could be included in the suite of modular components available for use with these devices. For example, various additional exemplary modules include, but are not limited to, an imaging module, a sensor module (including a pH, humidity, temperature, and/or pressure sensor), a stapler module, a UV light module, an X-ray module, a biopsy module, or a tissue collection module. It is understood that "module" is intended to encompass any modular component, including an arm or a body as discussed above.

In one embodiment, the mechanical and electrical couplings between the modular robotic sections are universal to help facilitate ease of assembly. That is, the couplings or connections are universal such that the various modules can be easily and quickly attached or removed and replaced with other modules. Connections can include friction fits, magnets, screws, locking mechanisms and sliding fitting. Alternatively, the connections can be any known connections for use in medical devices. In use, the couplings can be established by the surgeon or user according to one implementation. Alternatively, the couplings can be semi-automated such that the components are semi-self-assembling to improve timeliness.

Modular components need not be arms or other types of components having operational components or end effectors. According to various alternative embodiments, the modular components can be modular mechanical and electrical payload packages that can be used together in various combinations to provide capabilities such as obtaining multiple tissue samples, monitoring physiological parameters, and wireless command, control and data telemetry. It is understood that the modular payload components can be incorporated into all types of medical devices, including the various medical devices discussed and incorporated herein, such as magnetically controllable devices and/or wheeled devices similar to those disclosed in the applications incorporated above.

Figure 18A:
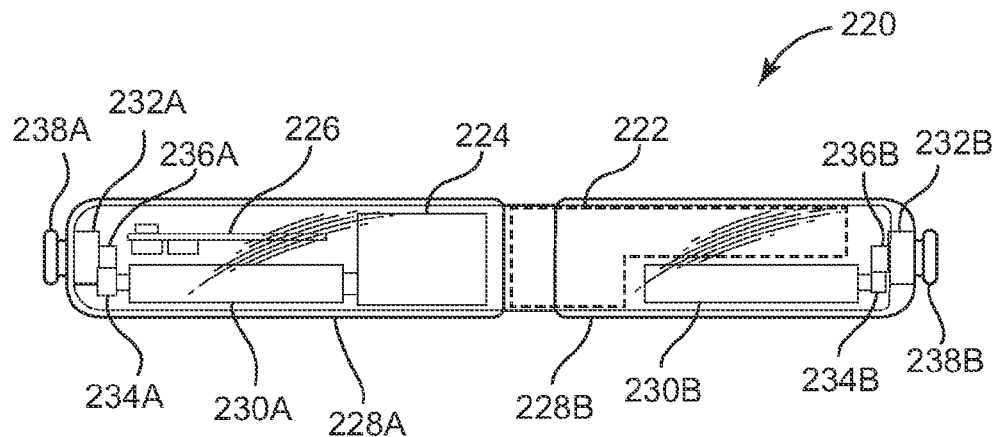
FIG. 18A is a front view of a modular medical device with a payload space, according to one embodiment.

FIG. 18A shows one embodiment of a device 220 having a payload area 222 that can accommodate various modular components such as environmental sensors, biopsy actuator system, and/or camera systems. More specifically, the payload area 222 is configured to receive any one of several modular components, including such components as the sensor, controller, and biopsy components discussed herein. It is understood that in addition to the specific modular components disclosed herein, the payload areas of the various embodiments could receive any known component to be added to a medical procedural device.

It is further understood that the robotic device having the payload area can be any known robotic device, including any device that is positioned substantially adjacent to or against a patient cavity wall (such as via magnetic forces), and is not limited to the robotic devices described in detail herein. Thus, while the robotic device embodiments depicted in FIGS. 18A and 18B (discussed below) are mobile devices having wheels, the various modular components described herein could just as readily be positioned or associated with a payload area in any other kind of robotic device or can further be used in other medical devices and applications that don't relate to robotic devices.

Returning to FIG. 18A, in this embodiment, the device is not tethered and is powered by an onboard battery 224. Commands can be sent to and from the device using an RF transceiver placed on a circuit board 226. Alternatively, the device 220 can be tethered and commands and power can be transmitted via the tether.

In the embodiment of FIG. 18A, the wheels 228A and 228B are powered by onboard motors 230A and 230B. Alternatively, the wheels 228A, 228B and other components can be actuated by any onboard or external actuation components. The wheels 228 in this implementation are connected to the motors 230 through a bearing 232 and a set of spur gears 234 and 236. Alternatively, any known connection can be used. The use of independent wheels allows for forward, reverse, and turning capabilities. In this embodiment, a small retraction ball 238 is attached to the outside of each wheel for retraction using a surgical grasper. Alternatively, no retraction component is provided. In a further alternative, any known retraction component can be included.

Figure 18B:
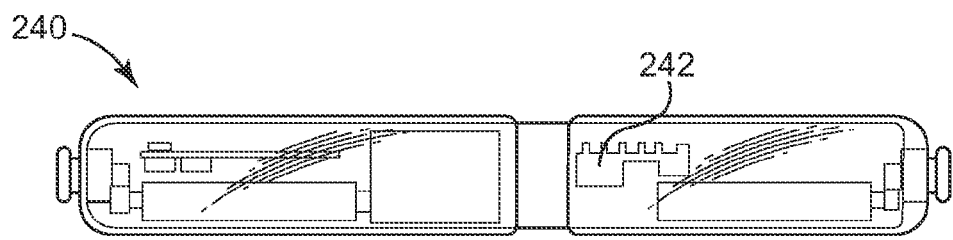
FIG. 18B is another front view of the device of FIG. 18A.

FIG. 18B shows yet another embodiment of a device 240 having a payload area 242. In this embodiment, the modular component in the payload area 242 is a sensor component. It is further understood that, according to various other implementations, more than one modular component can be positioned in the payload area 242 of this device 240 or any other device having a payload area. For example, the payload area 242 could include both a biopsy component and a sensor component, or both a biopsy component and a controller component. Alternatively, the payload area 242 could include any combination of any known functional components for use in procedural devices.

In accordance with one implementation, one component that can be included in the payload area 242 is a sensor package or component. The sensor package can include any sensor that collects and/or monitors data relating to any characteristic or information of interest. In one example, the sensor package includes a temperature sensor. Alternatively, the package includes an ambient pressure sensor that senses the pressure inside the body cavity where the device is positioned. In a further alternative, the package can include any one or more of a relative humidity sensor, a pH sensor, or any other known type of sensor for use in medical procedures.

The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

FIGS. 19A-24 depict a multi-segmented medical device 250, in accordance with one implementation. According to one embodiment, the device 250 is a robotic device 250 and further can be an in vivo device 250. This device embodiment 250 as shown includes three segments 252A, 252B, 254. Segments 252A and 252B are manipulator segments, while segment 254 is a command and imaging segment. Alternatively, the three segments can be any combination of segments with any combination of components and capabilities. For example, according to an alternative embodiment, the device could have one manipulator segment, one command and imaging segment, and a sensor segment. In a further alternative, the various segments can be any type of module, including any of those modules described above with respect to other modular components discussed herein.

Figure 19A:
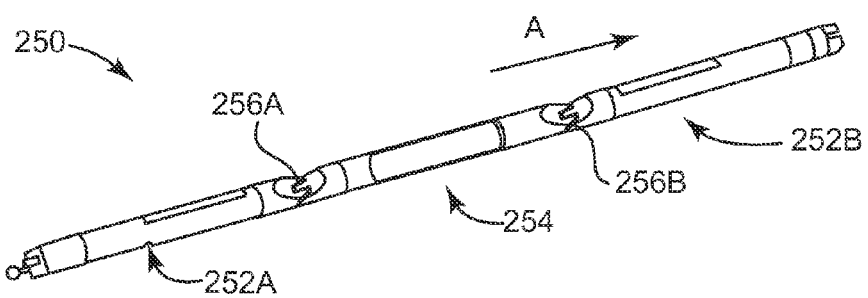
FIG. 19A is a perspective view of a modular medical device, according to another embodiment.
Figure 19B:
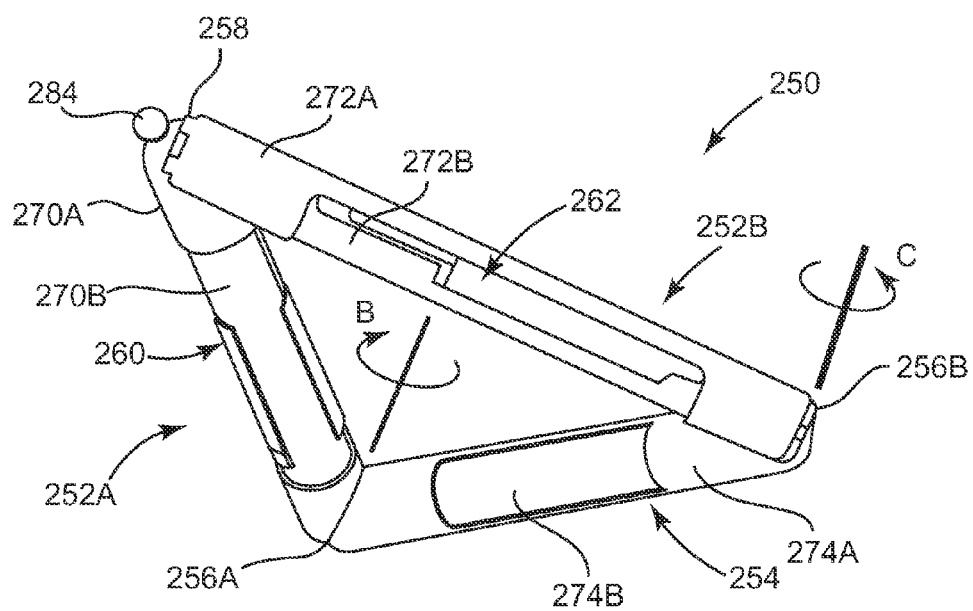
FIG. 19B is a perspective bottom view of the device of FIG. 19A.

As best shown in FIGS. 19A and 19B, segments 252A, 252B are rotatably coupled with the segment 254 via joints or hinges 256A, 256B. More specifically, segment 252A is rotatable relative to segment 254 about joint 256A around an axis as indicated by arrow B in FIG. 19B, while segment 252B is rotatable relative to segment 254 about joint 256B around an axis as indicated by arrow C in FIG. 19B.

In accordance with one embodiment, the device 250 has at least two configurations. One configuration is an extended or insertion configuration as shown in FIG. 19A in which the three segments 252A, 252B, 254 are aligned along the same axis. The other configuration is a triangle configuration as shown in FIG. 19B in which the manipulator segments 252A, 252B are each coupled to the segment 254 via the joints 256A, 256B and further are coupled to each other at a coupleable connection 258 at the ends of the segments 252A, 252B opposite the joints 256A, 256B.

Figure 20A:
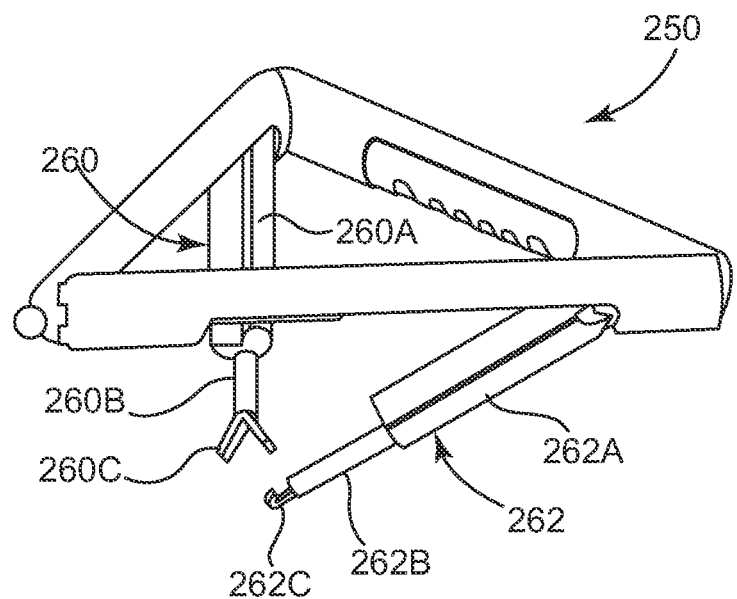
FIG. 20A is a perspective top view of the device of FIG. 19A.
Figure 21:
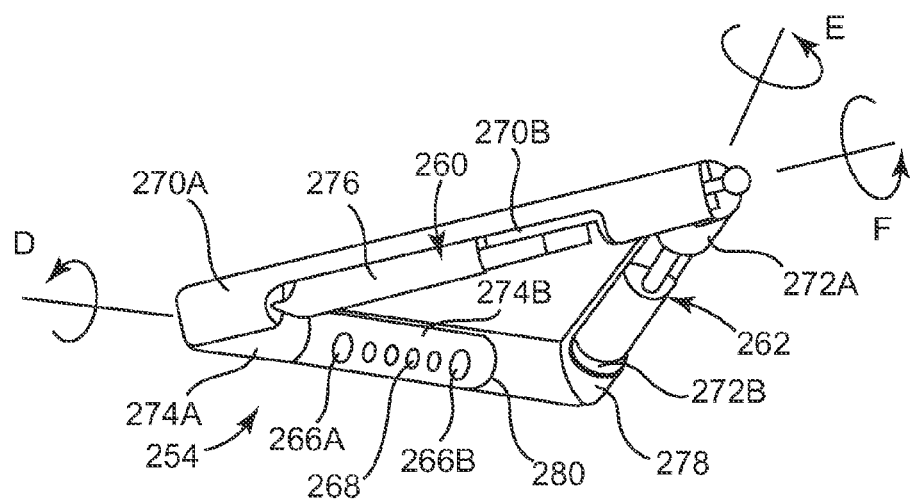
FIG. 21 is a perspective bottom view of the device of FIG. 19A.
Figure 22:
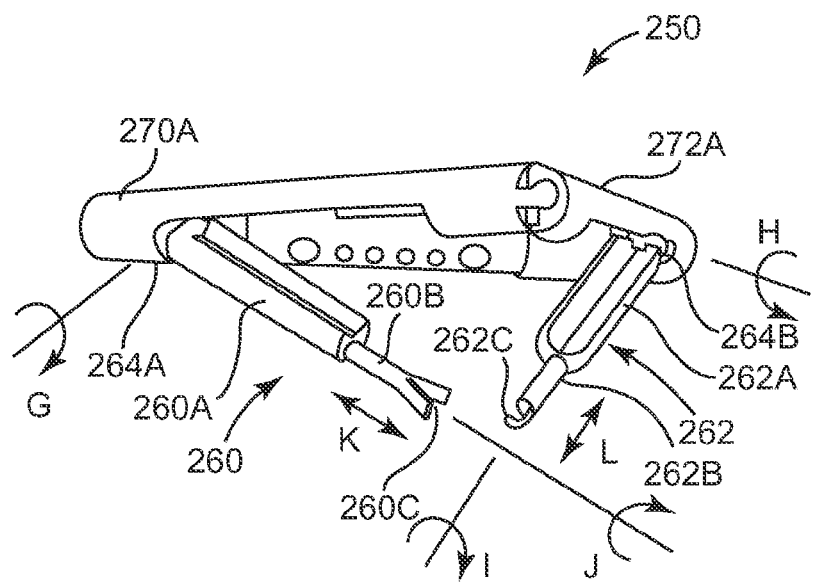
FIG. 22 is a perspective side view of the device of FIG. 19A.

As best shown in FIG. 20A, each of the manipulator segments 252A, 252B in this particular embodiment has an operational arm 260, 262 (respectively). Each arm 260, 262 is moveably coupled to its respective segment 252A, 252B at a joint 264A, 264B (respectively) (as best shown in FIG. 22). Further, segment 254 has a pair of imaging components (each also referred to herein as a "camera") 266A, 266B (as best shown in FIG. 21).

In one embodiment, each arm 260, 262 is configured to rotate at its joint 264A, 264B in relation to its segment 252A, 252B to move between an undeployed position in which it is disposed within its segment 252A, 252B as shown in FIG. 19B and a deployed position as shown in FIG. 20A. In one example, arm 260 is rotatable relative to segment 252A about joint 264A in the direction shown by G in FIG. 22, while arm 262 is rotatable relative to segment 252B about joint 264B in the direction shown by H in FIG. 22. Alternatively, the arms 260, 262 are moveable in relation to the segments 252A, 252B in any known fashion and by any known mechanism.

According to one embodiment as best shown in FIG. 20A, each arm 260, 262 has three components: a proximal portion 260A, 262A, a distal portion 260B, 262B, and an operational component 260C, 262C coupled with the distal portion 260B, 262B, respectively. In this embodiment, the distal portion 260B, 262B of each arm 260, 262 extends and retracts along the arm axis in relation to the proximal portion 260A, 262A while also rotating around that axis in relation to the proximal portion 260A, 262A. That is, distal portion 260B of arm 260 can move back and forth laterally as shown by the letter K in FIG. 22 and further can rotate relative to the proximal portion 260A as indicated by the letter J, while distal portion 262B of arm 262 can move back and forth laterally as shown by the letter L in FIG. 22 and further can rotate relative to the proximal portion 262A as indicated by the letter I.

In accordance with one implementation, the operational components 260C, 262C (also referred to herein as "end effectors") depicted in FIG. 20A are a grasper 260C and a cautery hook 262C. It is understood that the operational component(s) used with the device 250 or any embodiment herein can be any known operational component for use with a medical device, including any of the operational components discussed above with other medical device embodiments and further including any operational components described in the applications incorporated above. Alternatively, only one of the two arms 260, 262 has an operational component. In a further alternatively, neither arm has an operational component.

Alternatively, each arm 260, 262 comprises one unitary component or more than two components. It is further understood that the arms 260, 262 can be any kind of pivotal or moveable arm for use with a medical device which may or may not have operational components coupled or otherwise associated with them. For example, the arms 260, 262 can have a structure or configuration similar to those additional arm embodiments discussed elsewhere herein or in any of the applications incorporated above. In a further alternative, the device 250 has only one arm. In a further alternative, the device 250 has no arms. In such alternative implementations, the segment(s) not having an arm can have other components associated with or coupled with the segment(s) such as sensors or other types of components that do not require an arm for operation.

As discussed above, the segment 254 of the embodiment depicted in FIG. 21 has a pair of cameras 266A, 266B. Alternatively, the segment 254 can have a single camera or more than two cameras. It is understood that any known imaging component for medical devices, including in vivo devices, can be used with the devices disclosed herein and further can be positioned anywhere on any of the segments or on the arms of the devices.

In a further embodiment, the segment 254 as best shown in FIG. 21 can also include a lighting component 268. In fact, the segment 254 has four lighting components 268. Alternatively, the segment 254 can have any number of lighting components 268 or no lighting components. In a further alternative, the device 250 can have one or more lighting components positioned elsewhere on the device, such as one or both of segments 252A, 252B or one or more of the arms, etc.

In accordance with a further embodiment as best shown in FIGS. 19B and 21, each of the segments 252A, 252B, 254 has two cylindrical components—an outer cylindrical component and an inner cylindrical component—that are rotatable in relation to each other. More specifically, the segment 252A has an outer cylindrical component 270A and an inner cylindrical component 270B that rotates relative to the outer component 270A around an axis indicated by arrow F in FIG. 21.

Similarly, the segment 252B has an outer cylindrical component 272A and an inner cylindrical component 272B that rotates relative to the outer component 272A around an axis indicated by arrow E in FIG. 21. Further, the segment 254 has an outer cylindrical component 274A and an inner cylindrical component 274B that rotates relative to the outer component 274A around an axis indicated by arrow D in FIG. 21.

In use, the embodiments having rotatable cylindrical components as described in the previous paragraph can provide for enclosing any arms, cameras, or any other operational components within any of the segments. Further, any segment having such rotatable components provide for two segment configurations: an open configuration and a closed configuration. More specifically, segment 252A has an outer cylindrical component 270A with an opening 276 as shown in FIG. 21 through which the arm 260 can move between its deployed and undeployed positions. Similarly, segment 252B has an outer cylindrical component 272A with an opening 278 as shown in FIG. 21 through which the arm 262 can move between its deployed and undeployed positions. Further, segment 254 has an outer cylindrical component 274A with an opening 280 as shown in FIG. 21 through which the imaging component(s) 266A, 266B can capture images of a procedural or target area adjacent to or near the device 250.

FIG. 19B depicts the segments 252A, 252B, 254 in their closed configurations. That is, each of the inner cylindrical components 270B, 272B, 274B are positioned in relation to the respective outer cylindrical component 270A, 272A, 274A such that each opening 276, 278, 280, respectively, is at least partially closed by the inner component 270B, 272B, 274B such that the interior of each segment 252A, 252B, 254 is at least partially inaccessible from outside the segment.

More specifically, in the closed position, inner cylindrical component 270B of segment 252A is positioned in relation to outer cylindrical component 270A such that the arm 260 is at least partially enclosed within the segment 252A. According to one embodiment, the inner cylindrical component 270B is configured such that when it is in the closed position as shown in FIG. 19B, it closes off the opening 276 entirely. In a further embodiment, the inner cylindrical component 270B in the closed position fluidically seals the interior of the segment 252A from the exterior.

Similarly, in the closed position, inner cylindrical component 272B of segment 252B is positioned in relation to the outer cylindrical component 272A such that the arm 262 is at least partially enclosed within the segment 252B. According to one embodiment, the inner cylindrical component 272B is configured such that when it is in the closed position as shown in FIG. 19B, it closes off the opening 278 entirely. In a further embodiment, the inner cylindrical component 272B in the closed position fluidically seals the interior of the segment 252B from the exterior.

Further, in the closed position, inner cylindrical component 274B of segment 254 is positioned in relation to the outer cylindrical component 274A such that the imaging component(s) is not positioned within the opening 280. According to one embodiment, the inner cylindrical component 274B is configured such that when it is in the closed position as shown in FIG. 19B, the imaging component(s) and any lighting component(s) are completely hidden from view and not exposed to the exterior of the segment 254. In a further embodiment, the inner cylindrical component 274B in the closed position fluidically seals the interior of the segment 254 from the exterior.

In contrast, FIGS. 20A and 21 depict the segments 252A, 252B, 254 in their open configurations. In these configurations, each of the inner cylindrical components 270B, 272B, 274B are positioned such that the openings 276, 278, 280 are open.

In use, according to one embodiment, the inner cylindrical components 270B, 272B, 274B can thus be actuated to move between their closed and their open positions and thereby convert the device 250 between a closed or non-operational configuration (in which the operational components such as the arms 260, 262 and/or the imaging components 266 and/or the lighting components 268 are inoperably disposed within the segments 252A, 252B, 254) and an open or operational configuration (in which the operational components are accessible through the openings 276, 278, 280 and thus capable of operating). Thus, according to one implementation, the device 250 can be in its closed or non-operational configuration during insertion into a patient's body and/or to a target area and then can be converted into the open or operational configuration by causing the inner cylindrical components 270B, 272B, 274B to rotate into the open configurations.

Alternatively, one or more or all of the segments do not have inner and outer components that rotate in relation to each other.

It is understood that the various embodiments of the device 250 disclosed herein include appropriate actuation components to generate the force necessary to operate the arms and/or the rotatable cylinders in the segments. In one embodiment, the actuation components are motors. For example, segment 252A has a motor (not shown) operably coupled with the arm 260 and configured to power the movements of the arm 260. Similarly, segment 252B also has a motor (not shown) operably coupled with the arm 262 and configured to power the movements of the arm 260. In further embodiments, each of the segments 252A, 252B, 254 also have motors (not shown) operably coupled to one or both of the inner and outer cylinder of each segment to power the rotation of the cylinders in relation to each other. In one embodiment, each segment can have one motor to power all drivable elements (arms, cylinders, etc.) associated with that segment. Alternatively, a separate motor can be provided for each drivable element.

Figure 20B:
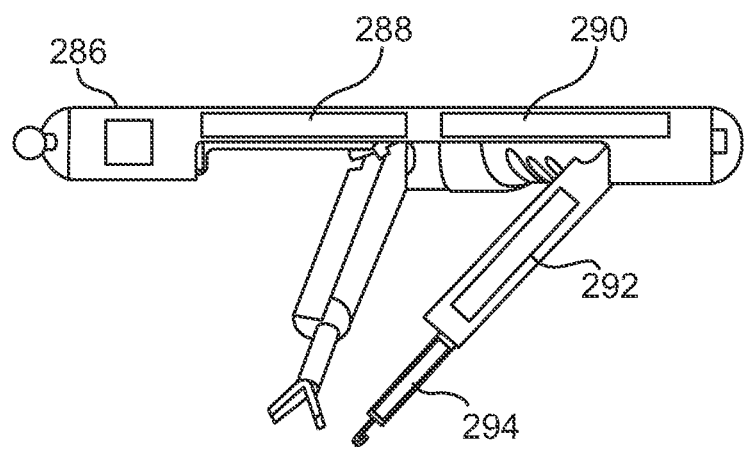
FIG. 20B is a perspective side view of the device of FIG. 19A.
Figure 20C:
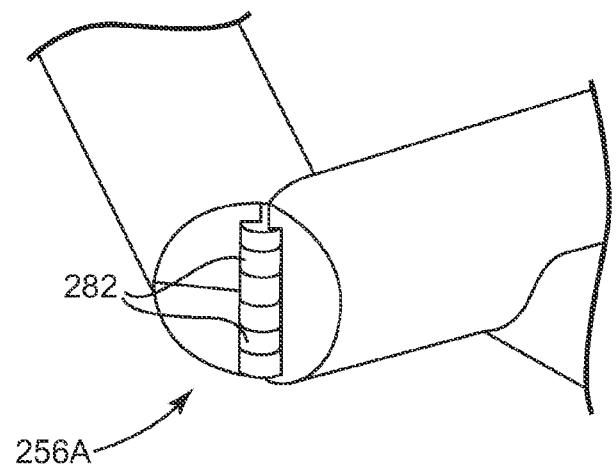
FIG. 20C is a perspective close-up view of a portion of the device of FIG. 19A.

In one embodiment, the joints 256A, 256B are configured to urge the segments 252A, 252B from the insertion configuration of FIG. 19A into the triangular configuration of FIG. 19B. That is, the joints 256A, 256B have torsion springs or some other known mechanism for urging the segments 252A, 252B to rotate around their joints 256A, 256B. For example, FIG. 20C depicts one embodiment in which the joint 256A has torsion springs 282 that are configured to urge segment 252A toward the triangular configuration.

In use, in accordance with one implementation, the device 250 in the insertion configuration as shown in FIG. 19A can be inserted into a patient's body through an incision, a trocar port, or natural orifice in the direction indicated by arrow A. Alternatively, the device 250 can be inserted in the other direction as well. After insertion and/or as the device 250 enters the target area or procedural area in the patient's body, the joints 256A, 256B with the torsion springs (or other standard mechanisms) urge the segments 252A, 252B from their insertion position to their triangular position. As the segments 252A, 252B contact each other to form joint 258, the two segments are coupled together with mating components that semi-lock the segments 252A, 252B together. That is, the two segments 252A, 252B can only be separated at the joint 258 by a force sufficient to overcome the semi-lock. Any such known mating component or coupling component, including any mechanical or magnetic mating component(s), can be incorporated into the device 250 for this purpose.

Thus, according to one embodiment, the device 250 can be in its insertion configuration during insertion into the patient. As the device 250 enters the target cavity and exits the port or incision, the torsion springs or other mechanisms at the joints 256A, 256B cause the two segments 252A, 252B to move toward each other until they couple to form the triangular configuration. The device 250 can then be attached to the abdominal wall by some method such as an external magnetic handle. Alternatively, the device 250 can be positioned anywhere in the cavity of the patient as desired by the user. The device 250 is then used to perform some sort of procedure.

Subsequently, when the procedure is complete, the device 250 can be retracted from the cavity. To do so, the surgeon uses a grasping or retrieval tool such as a Endo Babcock grasper made by Covidien in Mansfield, Mass., to attach to or otherwise grasp the ball 284 at the joint 258 and apply sufficient force to overcome the semi-lock of the joint 258. Alternatively, any retrieval component can be positioned at the end of segment 252A or elsewhere on the device 250 for grasping or otherwise coupling to for purposes of removing the device 250 from the patient's body. When the coupling of the semi-lock is overcome, the force urges the segments 252A, 252B away from each other, thereby making it possible for the surgeon to pull the ball 284 through a port or incision and out of the patient, thereby forcing the device 250 into its insertion configuration.

The multiple segments provided in the various embodiments of the device disclosed herein result in significantly more payload space than a single cylindrical body. The increased payload space results in increased capabilities for the device in the form of more, bigger, or more complex operational components, more, bigger, or more complex motors, magnets (as described below) and other similar benefits relating to the availability of more space for more, bigger, or more complex components. For example, FIG. 20B depicts a side view of the device 250 according to one embodiment that shows the payload space available in segment 252B. More specifically, segment 252B and its coupled arm 262 have payload spaces 286, 288, 290, 292, 294 that can be used to accommodate motors, operational components, sensors, magnets (as described below) or any other type of component that could be useful for a procedural device. Similarly, each segment 252A, 252B, 254 can have such payload spaces. In addition, the segments 252A, 252B, 254 allow for maximization of the payload space available across the segments 252A, 252B, 254 by distributing the components such as motors, operational components, or magnets to maximize their effectiveness while minimizing the amount of space required by each such component. For example, it might maximize effectiveness of the device 250 while minimizing the utilized space to have one large motor in one segment that provides force for operation of components in more than one segment.

It is understood that various embodiments of the segmented devices disclosed herein are in vivo devices that can be inserted into and positioned within a patient's body to perform a procedure. In one embodiment, an external controller is also provided that transmits signals to the device 250 to control the device 250 and receives signals from the device 250. In one embodiment, the controller communicates with the device 250 wirelessly. Alternatively, the controller and the device 250 are coupled via a flexible communication component such as a cord or wire (also referred to as a "tether") that extends between the device 250 and the controller.

Figure 23:
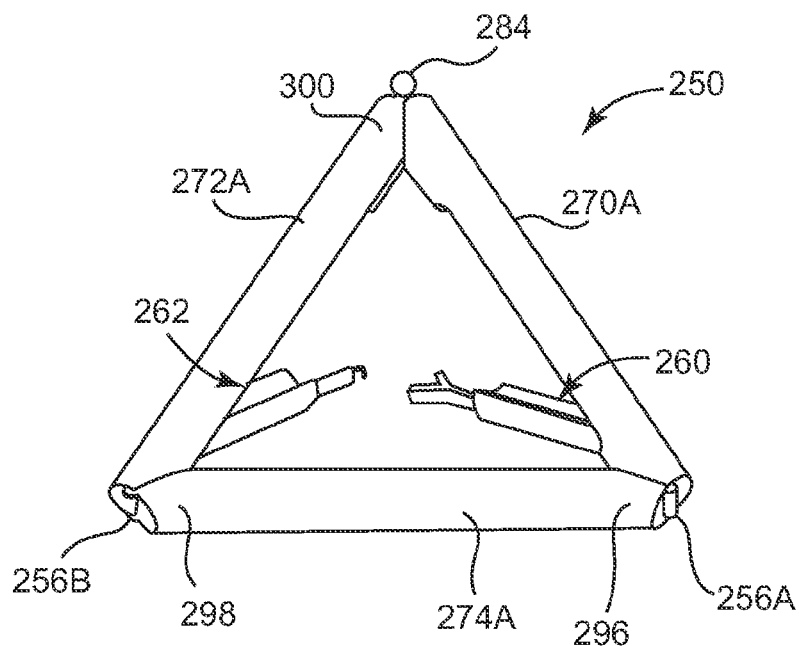
FIG. 23 is a top view of the device of FIG. 19A.

It is also understood that various embodiments of the devices disclosed herein can be used in conjunction with known attachment components to attach or otherwise position the device near, against, or adjacent to an interior cavity wall inside the patient. In one embodiment, the attachment components are one or more magnets, disposed within the device, that communicate magnetically with one or more magnets positioned outside the patient's body. The device magnets can be positioned on or in the device in any suitable configuration. For example, the device magnets in one embodiment can be positioned within the segments 252A, 252B, 254 at positions 296, 298, 300 as shown in FIG. 23. It is understood that the external magnets can be used outside the body to position and/or move the device 250 inside the body.

Figure 24:
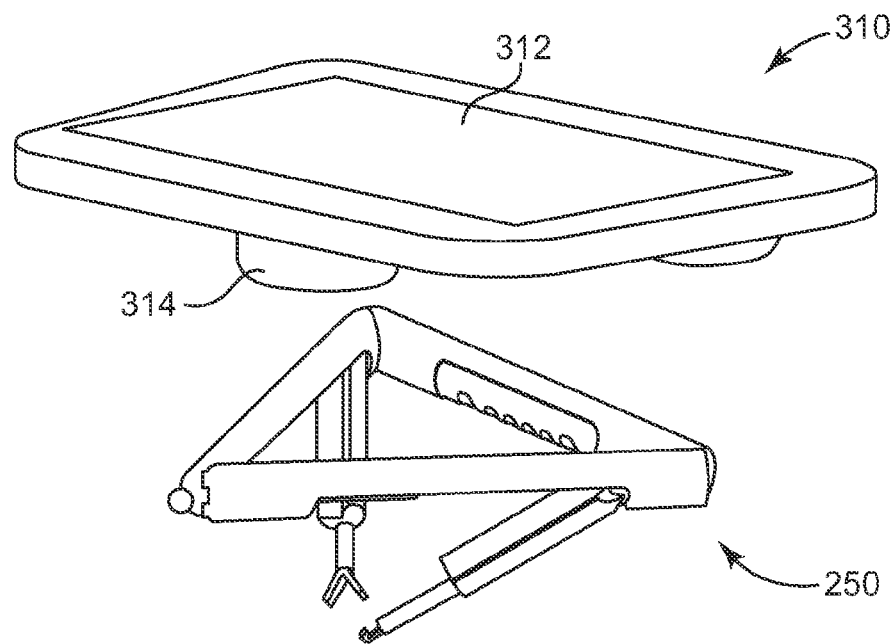
FIG. 24 is a perspective view of modular medical device control and visualization system, according to one embodiment.

It is further understood that various embodiments of the devices disclosed herein can be used in conjunction with known visualization and control components, such as the console 310 depicted in FIG. 24. The console 310 has a display 312 and magnets 314 and is positioned outside the patient such that the magnets 314 can be in magnetic communication with the device magnets (not shown) disposed within or otherwise coupled with the device 250. The console 310 can be used to move the device 250 by moving the console 310 outside the body such that the device 250 is urged to move inside the body, because the console magnets 250 are magnetically coupled with the device magnets (not shown) within the device 250 such that the device 250 remains substantially fixed in relation to the console 310. In addition, it is understood that the triangular (and quandrangular) devices disclosed and described in relation to FIGS. 19A-25 can be used in conjunction with any of the external controller or visualization components and systems disclosed and discussed above and in the applications incorporated above.

The segmented device 250, according to one embodiment, provides greater stability and operability for the device 250 in comparison to other in vivo devices. That is, a device having more than one segment such as device 250 provides for a configuration with a larger "footprint" for the device 250, thereby resulting in greater stability and leverage during use of the device 250. For example, the device 250 with the triangular configuration in FIG. 24 that is urged against the interior cavity wall of the patient by the console magnets 314 has greater stability and leverage in comparison to a device that has a smaller "footprint." That is, the device 250 can have at least three magnets (not shown) disposed at the three corners of the triangular configuration such that when the device 250 is magnetically positioned against the interior cavity wall, the arms of the device 250 can apply greater force to the target tissues while maintaining the position of the device 250 than a corresponding single cylindrical device body.

Figure 25:
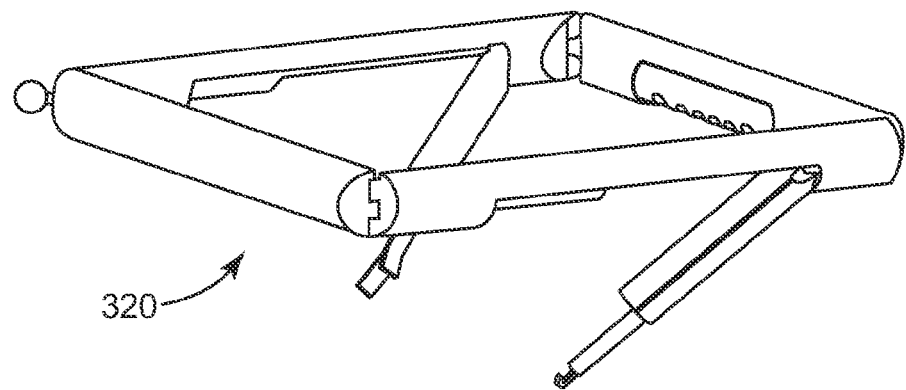
FIG. 25 is a perspective view of a modular medical device, according to one embodiment.

It is understood that the device embodiments disclosed herein are not limited to a triangular configuration. FIG. 25 depicts a device 320 having a quadrangular configuration with four segments. Similarly, devices are contemplated herein having any number of segments ranging from two segments to any number of segments that can be used for a device that can be positioned inside a patient's body. For example, a device incorporating the components and structures disclosed herein could have six or eight segments or more.

In accordance with one embodiment, the various medical devices disclosed herein and in the applications incorporated above can be used cooperatively. That is, two or more devices can be used at the same time during the same procedure to accomplish more or perform the procedure more quickly than when only one device is used at a time. As such, multiple robots (more than one device and up to any number capable of being inserted into a patient's cavity and present in the cavity at the same time for performing one or more procedures) are inserted into the patient's cavity and each controlled by the surgical team.

Figure 26:
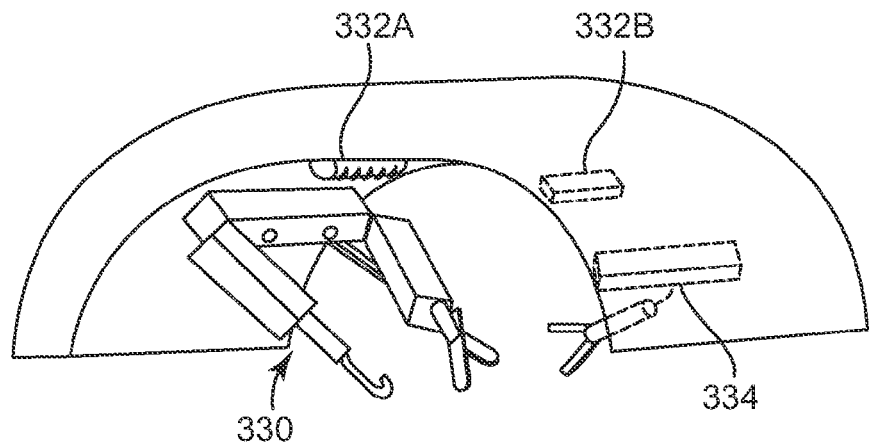
FIG. 26 is a perspective cutaway view of various medical devices operating cooperatively in a body cavity, according to one embodiment.
Figure 27:
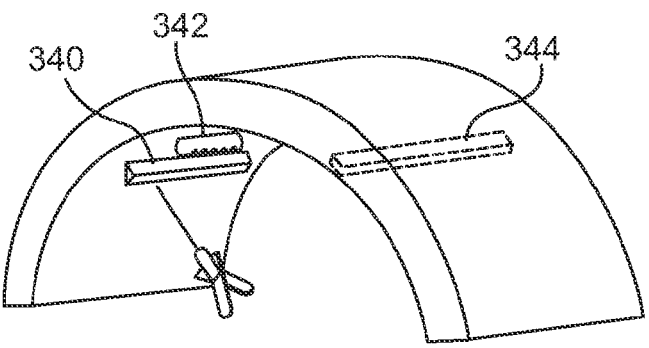
FIG. 27 is a perspective cutaway view of various medical devices operating cooperatively in a body cavity, according to another embodiment.
Figure 28:
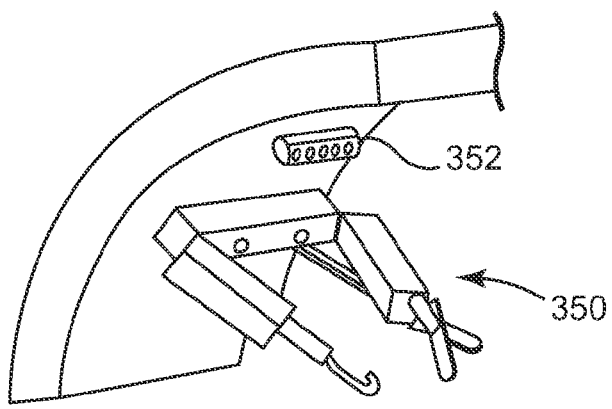
FIG. 28 is a perspective cutaway view of various medical devices operating cooperatively in a body cavity, according to a further embodiment.

FIGS. 26-28 depict three different embodiments of cooperative use of two or more medical devices together. In FIG. 26, the devices that are positioned with a cavity of a patient include a device with operational arms 330, two lighting devices 332A, 332B, and a cylindrical device having a winch component with an end effector 334. These devices can be operated at the same time using one or more external controllers and/or visualization components according to the various embodiments disclosed above or in the applications incorporated above.

Similarly, FIG. 27 depicts a cooperative procedure implementation using a cylindrical device having a winch component with an end effector 340, a lighting device 342, and a cylindrical device 344. The cylindrical device 344 can have an imaging component and/or additional operational components such as sensors, etc.

Another embodiment is depicted in FIG. 28, in which a cooperative procedure is performed using a device with arms 350 and a lighting device 352.

According to one embodiment, the devices are assembled while being introduced through a natural orifice, a port, or an incision. For instance, if insertion is through the esophagus, each robot is inserted down the overtube, which provides an "in line" ability for consistent assembly as each robot is "pushed" down the overtube. Alternatively, after insertion into the abdominal cavity, a camera and tool can be inserted to assist with the mechanical connections, or other robotic devices can be used to help with the mechanical connections.

The level of cooperation amongst two or more in vivo medical devices varies between high network communications, planning, and some autonomy, to lower level mechanical connections and surgeon control. That is, in certain embodiments, the cooperative devices can communicate with each other and perform with some level of autonomy (without input or with limited input from the user or surgeon). In an alternative implementation, the cooperative devices can simply be positioned in the same general procedural space and separately controlled by one or more users to work cooperatively to perform a procedure or procedures.

In one embodiment, two or more devices positioned in a body cavity can be coupled to each other in some fashion. It is understood that the coupling does not necessarily result in a rigidly coupling of the devices to each other in all degrees. As such, the configuration(s) of two or more devices may adapt to the varying geometry of each patient, disturbances to the abdominal wall, and respiration cycle. According to one implementation, one benefit of coupling the devices is to maintain a set distance between the devices for vision, lighting, tissue manipulation, and other procedural purposes.

Although the present invention has been described with reference to preferred embodiments, persons skilled in the art will recognize that changes may be made in form and detail without departing from the spirit and scope of the invention.

What is claimed is:

1. A modular medical device system, the system comprising:
   (a) a first modular component configured to be disposed inside a cavity of a patient, the first modular component comprising:
      (i) a first body;
      (ii) a first operational component operably coupled to the first body;
      (iii) at least one first actuator disposed within the first body or the first operational component, wherein the at least one first actuator is configured to actuate the first body or the first operational component; and
      (iv) at least one first coupling component associated with the first body; and
   (b) a second modular component configured to be disposed inside a cavity of a patient, the second modular component comprising:
      (i) a second body;
      (ii) a second operational component operably coupled to the second body; and
      (iii) at least one second coupling component associated with the second body, the at least one second coupling component configured to be coupleable with the at least one first coupling component; and
   (c) a third modular component configured to be disposed inside a cavity of a patient, the third modular component comprising:
      (i) a third body;
      (ii) a third operational component operably coupled to the third body; and
      (iii) at least one third coupling component associated with the third body, the at least one third coupling component configured to be coupleable with the at least one first coupling component and the at least one second coupling component.

2. The system of claim 1, wherein the third operational component is chosen from a group consisting of an imaging component, an operational arm component, a sensor component, and a lighting component.

3. The system of claim 1, wherein the third modular component is disposed between the first and second modular components, wherein the third operational component comprises an imaging component, wherein the first and second operational components comprise operational arm components.

4. The system of claim 1, wherein the first, second, and third modular components are coupled in a triangular configuration, wherein the third operational component comprises an imaging component, wherein the first and second operational components comprise operational arm components.

5. A modular medical device system, the system comprising:
   (a) a first modular component configured to be disposed inside a cavity of a patient, the first modular component comprising:
      (i) a first body;
      (ii) a first arm operably coupled to the first body;
      (iii) a first end effector operably coupled to the first arm; and
      (iv) at least one first coupling component associated with the first body;
   (b) a second modular component configured to be disposed inside a cavity of a patient, the second modular component comprising:
      (i) a second body;
      (ii) a second arm operably coupled to the second body;
      (iii) a second end effector operably coupled to the second arm; and
      (iv) at least one second coupling component associated with the second body, the at least one second coupling component configured to be coupleable with the at least one first coupling component; and (c) a third modular component positioned between the first and second modular components, the third modular component comprising:
(i) a third body; and
(iii) at least one third coupling component associated with the third body, the at least one third coupling component configured to be coupleable with the at least one first coupling component and the at least one second coupling component.

6. The system of claim 5, wherein the third modular component further comprises a first imaging component operably coupled to the third body.

7. The system of claim 6, wherein the third modular component further comprises at least one operational component chosen from a group consisting of a second imaging component, a sensor component, and a lighting component.

8. The system of claim 5, wherein the first end effector comprises a cautery component and the second end effector comprises a grasper.

9. The system of claim 5, further comprising an external controller configured to be positioned outside the cavity of the patient, the external controller being operably coupled to at least one of the first, second, and third modular components via a connection component.

10. The system of claim 9, wherein the external controller comprises at least one arm controller component operably coupled to the first and second arms.

11. The system of claim 9, wherein the external controller comprises an image display component operably coupled to the first imaging component via the connection component.

12. The system of claim 5, wherein the first and second bodies are coupled to the third body such that a combination body is formed, wherein the first arm is coupled to the first body at a first end of the combination body and the second arm is coupled to the second body at a second end of the combination body.

13. A method of performing a medical procedure with a modular medical device system, the method comprising:
forming an incision accessing a cavity of a patient;
inserting a first modular component into the cavity through the incision, the first modular component comprising:
(a) a first body;
(b) a first operational arm component operably coupled to the first body; and
(c) at least one first coupling component associated with the first body;
inserting a second modular component into the cavity through the incision, the second modular component comprising:
(a) a second body;
(b) a second operational arm component operably coupled to the second body; and
(c) at least one second coupling component associated with the second body, the at least one second coupling component configured to be coupleable with the at least one first coupling component;
positioning a third modular component through the incision, the third modular component comprising:
(a) a third body; and
(b) at least one third coupling component associated with the third body, the at least one third coupling component configured to be coupleable with the at least one first coupling component and the at least one second coupling component; and
coupling the at least one first coupling component and the at least one second coupling component to the at least one third coupling component while the first, second, and third modular components are positioned through the incision.

14. The method of claim 13, whereby the third modular component is positioned between the first and second modular components.

15. The method of claim 13, further comprising controlling the modular medical device system with a controller operably coupled to at least one of the first, second, or third modular components via a connection component.

16. The method of claim 13, further comprising, after completing the medical procedure, uncoupling the at least one first coupling component and the at least one second coupling component from the at least one third coupling component and removing the first, second, and third modular components through the incision.

17. The system of claim 1, wherein the first operational component is chosen from a group consisting of an imaging component, an operational arm component, a sensor component, and a lighting component.

18. The system of claim 1, wherein the second operational component is chosen from a group consisting of an imaging component, an operational arm component, a sensor component, and a lighting component.

19. The system of claim 1, further comprising an external controller configured to be positioned outside the cavity of the patient, the external controller being operably coupled to at least one of the first, second, and third modular components via a connection component.

20. The system of claim 1, wherein the first and second bodies are coupled to the third body such that a combination body is formed, wherein the first operational component comprises a first operational arm component coupled to the first body at a first end of the combination body and the second operational component comprises a second operational arm coupled to the second body at a second end of the combination body.

* * * * *